United States Patent
Haap et al.

(10) Patent No.: US 10,689,339 B2
(45) Date of Patent: Jun. 23, 2020

(54) PYRROLIDINE DERIVATIVES

(71) Applicant: Hoffmann-La Roche Inc., Little Falls, NJ (US)

(72) Inventors: Wolfgang Haap, Basel (CH); Bernd Kuhn, Basel (CH); Thomas Luebbers, Basel (CH); Jens-Uwe Peters, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/111,721

(22) Filed: Aug. 24, 2018

(65) Prior Publication Data

US 2018/0362461 A1  Dec. 20, 2018

Related U.S. Application Data

(63) Continuation of application No. PCT/EP2017/053967, filed on Feb. 22, 2017.

(30) Foreign Application Priority Data

Feb. 26, 2016 (EP) ..................... 16157679

(51) Int. Cl.

| | |
|---|---|
| *C07D 207/16* | (2006.01) |
| *C07D 403/12* | (2006.01) |
| *C07D 403/14* | (2006.01) |
| *C07D 401/12* | (2006.01) |
| *C07D 417/12* | (2006.01) |
| *C07D 413/12* | (2006.01) |
| *C07D 405/12* | (2006.01) |
| *A61P 3/10* | (2006.01) |
| *A61P 9/10* | (2006.01) |
| *A61P 27/02* | (2006.01) |
| *A61P 35/00* | (2006.01) |

(52) U.S. Cl.
CPC .............. *C07D 207/16* (2013.01); *A61P 3/10* (2018.01); *A61P 9/10* (2018.01); *A61P 27/02* (2018.01); *A61P 35/00* (2018.01); *C07D 401/12* (2013.01); *C07D 403/12* (2013.01); *C07D 403/14* (2013.01); *C07D 405/12* (2013.01); *C07D 413/12* (2013.01); *C07D 417/12* (2013.01)

(58) Field of Classification Search
CPC .. C07D 207/16; C07D 401/12; C07D 403/12; C07D 403/14; C07D 405/12; C07D 413/12; C07D 417/12; A61P 27/02; A61P 9/10; A61P 3/10; A61P 35/00
USPC .......................................................... 514/423
See application file for complete search history.

(56) References Cited

FOREIGN PATENT DOCUMENTS

| WO | 2010/121918 A1 | 10/2010 |
|---|---|---|
| WO | 2013/068434 A1 | 5/2013 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Aikawa et al., "Arterial and aortic valve calcification abolished by elastolytic cathepsin S deficiency in chronic renal disease" Circulation 119(13):1785-94 (Apr. 2009).
Bromme, D. Current Protocols in Protein Science "Papain-like cystein proteases" 2001: vol. Chapter 21:Unit 21.2.
Burden et al., "Antibody-mediated inhibition of cathepsin S blocks colorectal tumor invasion and angiogenesis" Clin Cancer Res. 15(19):6042-51 (Oct. 2009).
Burns-Kurtis, "Cathepsin S expression is up-regulated following balloon angioplasty in the hypercholesterolemic rabbit" Cardiovasc Res. 62(3):610-20 (Jun. 2004).
Cheng et al., "Increased expression of elastolytic cysteine proteases, cathepsins S and K, in the neointima of balloon-injured rat carotid arteries" Am J Pathol. 164(1):243-51 ( 2004).

(Continued)

*Primary Examiner* — Kristin A Vajda
(74) *Attorney, Agent, or Firm* — Bradley E. Davis

(57) ABSTRACT

The invention relates to a compound of formula (I)

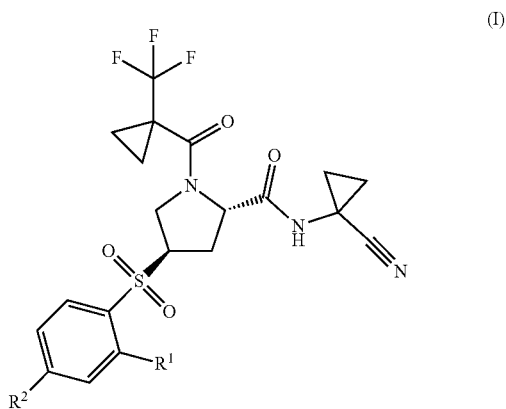

wherein R¹ and R² are defined as in the description and in the claims. The compound of formula (I) can be used as a medicament.

16 Claims, No Drawings

(56) References Cited

OTHER PUBLICATIONS

De Nooijer, "Leukocyte cathepsin S is a potent regulator of both cell and matrix turnover in advanced atherosclerosis" Arterioscler Thromb Vasc Biol. 29(2):188-94 (Feb. 2009).
Driessen et al., "Cathepsin S controls the trafficking and maturation of MHC class II molecules in dendritic cells" J Cell Biol. 147(4):775-90 (Nov. 1999).
Hilpert et al., "Identification of Potent and Selective Cathepsin S Inhibitors Containing Different Central Cyclic Scaffolds" Journal of Medicinal Chemistry 56(23):9789-9801 (Dec. 12, 2013).
Hsing and Rudensky, "The lysosomal cysteine proteases in MHC class II antigen presentation" Immunol Rev. 207:229-41 (Oct. 2005).
Liu et al., "Increased serum cathepsin S in patients with atherosclerosis and diabetes" Atherosclerosis 186(2):411-9 (Jun. 2006).
PCT ISR and Written Opinion for PCT/EP2017/053967, dated 2017.
Roberts, R., "Lysosomal cysteine proteases: structure, function and inhibition of capthepsins" Drug News & Perspectives 18(10):605-614 (2005).
Rodgers et al., "Destabilizing role of cathepsin S in murine atherosclerotic plaques" Arterioscler Thromb Vasc Biol. 26(4):851-6 (Apr. 2006).
Rudensky and Beers, "Lysosomal cysteine proteases and antigen presentation" Ernst Schering Res Found Workshop 56:81-95 (2006).
Shi et al., "Deficiency of the cysteine protease cathepsin S impairs microvessel growth" Circ Res. 92(5):493-500 (Mar. 2003).
Sukhova et al., "Deficiency of cathepsin S reduces atherosclerosis in LDL receptor-deficient mice" J Clin Invest. 111(6):897-906 (2003).
Sukhova et al., "Expression of the elastolytic cathepsins S and K in human atheroma and regulation of their production in smooth muscle cells" J Clin Invest. 102(3):576-83 (Aug. 1998).
Wang, "J Biol Chem." Cathepsin S controls angiogenesis and tumor growth via matrix-derived angiogenic factors 281(9):6020-9 (Mar. 2006).
Williams et al., "Role of cathepsin S in ozone-induced airway hyperresponsiveness and inflammation" Pulm Pharmacol Ther. 22(1):27-32 (Feb. 2009).

* cited by examiner

PYRROLIDINE DERIVATIVES

RELATED APPLICATIONS

This application is a continuation of International Application No. PCT/EP2017/053967, filed Feb. 22, 2017, claiming priority to EP16157679.8, filed Feb. 26, 2016, each of which are incorporated herein by reference in its entirety.

The present invention relates to organic compounds useful for therapy and/or prophylaxis in a mammal, and in particular to compounds that are preferential inhibitors of the cysteine protease cathepsin, in particular of the cysteine protease cathepsin S.

The invention relates in particular to a compound of formula (I)

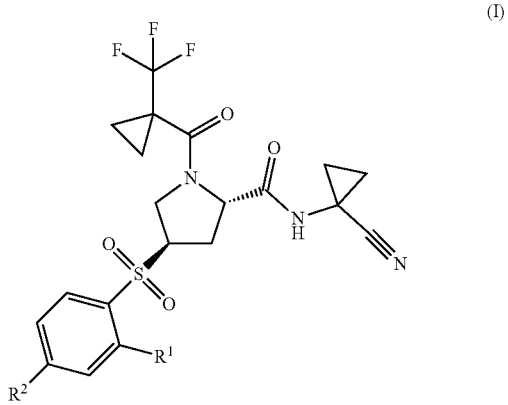

wherein
$R^1$ is hydrogen, alkyl, haloalkyl, halogen or triazolyl; and
$R^2$ is (halo)(oxy)pyridinyl, (alkyl)(oxy)pyridinyl, (alkyl)(haloalkyl)pyrazolyl, haloalkoxyphenyl, alkoxyphenyl, cycloalkyloxyphenyl, cycloalkyloxy, alkyltetrazolyl, triazolyl, alkyltriazolyl, dialkyltriazolyl, halotriazolyl, haloalkylpyrazolyl, formylphenyl, aminopyrimidinyl, cyanophenyl, (alkoxy)(dihalo)phenyl, hydroxyalkylphenyl, benzo[1,3]dioxolyl, dialkylthiazolyl, alkylthiazolyl, alkoxypyrimidinyl, dialkylisoxazolyl or (halo)(haloalkyl)triazolyl;
or a pharmaceutically acceptable salt or ester thereof.

The compounds of the invention are preferential inhibitors of the cysteine protease Cathepsin (Cat), in particular Cathepsin S and are therefore useful to treat metabolic diseases like diabetes, atherosclerosis, abdominal aortic aneurysm, peripheral arterial disease, cancer, reduction of cardiovascular events in chronic kidney disease and diabetic nephropathy. In addition, immune mediated diseases like rheumatoid arthritis, multiple sclerosis, sjorgen syndrome, lupus erythematosus, neuropathic pain, diabetes type I, asthma and allergy and skin related immune disease are suitable diseases to be treated with a cathepsin S inhibitor.

Objects of the present invention are the compounds of formula (I) and their aforementioned salts per se and their use as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells. (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/ln APO-E deficient mice a strong reduction of accelerated calcification is seen on top of the anti atherosclerotic activity in arteries and heart valves (Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova, G. K., et al. (2003), 'Deficiency of cathepsin S reduces atherosclerosis in LDL receptor-deficient mice', J Clin Invest, 111 (6), 897-906). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of Tcells to the chronic inflammation of the atherosclerotic tissue. Elevated inflammation results in further oxidative and proteolytic tissue damage and subsequently plaque destabilisation (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MHC class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyperresponsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500; Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. A particular example of alkyl is methyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of "cycloalkyl" is cyclopropyl.

The term "oxy", alone or in combination, signifies the —O— group.

As an exception, "(oxy)pyridinyl" refers to py$^+$-O$^-$, wherein py represents pyridine.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular "alkoxy" are methoxy and ethoxy, and in particular methoxy.

The term "cycloalkyloxy", alone or in combination, signifies a group of the formula cycloalkyl-O— in which the term "cycloalkyl" has the previously given significance. A particular cycloalkyloxy is cyclopropyloxy.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. A particular "halogen" is chlorine.

The term "haloalkyl", alone or in combination, denotes an alkyl group substituted with at least one halogen, particularly substituted with one to five halogens, particularly one to three halogens. Particular "haloalkyl" are trifluoromethyl and difluoromethyl, in particular trifluoromethyl.

The term "haloalkoxy", alone or in combination, denotes an alkoxy group substituted with at least one halogen, particularly substituted with one to five halogens, particularly one to three halogens. Particular "haloalkoxy" is trifluoromethoxy.

The terms "hydroxyl" and "hydroxy", alone or in combination, signify the —OH group.

The term "carbonyl", alone or in combination, signifies the —C(O)— group.

The term "formyl", alone or in combination, signifies the —CH(O) group

The term "amino", alone or in combination, signifies the primary amino group (—NH$_2$), the secondary amino group (—NH—), or the tertiary amino group (—N—).

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention further relates to:

A compound of formula (I) wherein $R^1$ is alkyl, haloalkyl or halogen;

A compound of formula (I) wherein $R^1$ is methyl, trifluoromethyl or chlorine;

A compound of formula (I) wherein $R^2$ is (alkyl)(haloalkyl)pyrazolyl, alkyltetrazolyl, triazolyl, alkyltriazolyl, dialkyltriazolyl, halotriazolyl, haloalkylpyrazolyl, dialkylthiazolyl, alkylthiazolyl or dialkylisoxazolyl;

A compound of formula (I) wherein $R^2$ is (methyl)(trifluoromethyl)pyrazolyl, methyltetrazolyl, triazolyl, methyltriazolyl, dimethyltriazolyl, chlorotriazolyl, trifluoromethylpyrazolyl, difluoromethylpyrazolyl, dimethylthiazolyl, methylthiazolyl or dimethylisoxazolyl;

The invention further relates to a compound of formula (I) selected from:

(2S,4R)-4-[4-(2-Chloro-1-oxy-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(2-Methyl-1-oxy-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(2-Methyl-5-trifluoromethyl-2H-pyrazol-3-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-(2'-Trifluoromethoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;

(2S,4R)-4-(2'-Ethoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;

(2S,4R)-4-(2'-Cyclopropoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;

(2S,4R)-4-(4-Cyclobutoxy-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(2-chloro-4-(5-methyl-2H-tetrazol-2-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(5-methyl-1H-tetrazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(2,4-di(1H-1,2,4-triazol-1-yl)phenylsulfonyl)-1-(1-(trifluoromethyl)cyclopropanecarbonyl)pyrrolidine-2-carboxamide;

(2S,4R)-4-(2-chloro-4-(2H-1,2,3-triazol-2-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(1H-1,2,3-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3,5-dimethyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3-chloro-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3-(trifluoromethyl)-1H-pyrazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(5-methyl-3-(trifluoromethyl)-1H-pyrazol-1-yl)phenylsulfonyl)-N-(1-cyanocyclopropyl)-1-(1-(trifluoromethyl) cyclopropanecarbonyl)pyrrolidine-2-carboxamide;

(2S,4R)—N-(1-cyanocyclopropyl)-4-(2-methyl-4-(3-(trifluoromethyl)-1H-pyrazol-1-yl)phenyl sulfonyl)-1-(1-(trifluoromethyl)cyclopropanecarbonyl)pyrrolidine-2-carboxamide;

(2S,4R)—N-(1-cyanocyclopropyl)-4-(2'-(trifluoromethoxy)biphenyl-4-ylsulfonyl)-1-(1-(trifluoromethyl)cyclopropanecarbonyl)pyrrolidine-2-carboxamide;

(2S,4R)-4-(2-chloro-4-cyclobutoxyphenylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(3-methyl-2'-(trifluoromethoxy)biphenyl-4-ylsulfonyl)-1-(1-(trifluoromethyl)cyclopropanecarbonyl)pyrrolidine-2-carboxamide;

(2S,4R)-4-[4-(5-Methyl-3-trifluoromethyl-pyrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(3-Methyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(3-Methyl-[1,2,4]triazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-(4-(1H-1,2,4-triazol-1-yl)-2-(trifluoromethyl)phenylsulfonyl)-N-(1-cyanocyclopropyl)-1-(1-(trifluoromethyl)cyclopropanecarbonyl)pyrrolidine-2-carboxamide (2S,4R)-4-[4-(3,5-Dimethyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(1-methyl-3-(trifluoromethyl)-1H-pyrazol-5-yl)phenyl sulfonyl)-1-(1-(trifluoromethyl)cyclopropanecarbonyl)pyrrolidine-2-carboxamide;

(2S,4R)—N-(1-cyanocyclopropyl)-4-(2'-formyl-3-methyl-biphenyl-4-ylsulfonyl)-1-(1-(trifluoromethyl)cyclopropanecarbonyl)pyrrolidine-2-carboxamide;

(2S,4R)-4-[4-(3-Chloro-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(5-methyl-1H-1,2,4-triazol-1-yl)-2-(trifluoromethyl)phenylsulfonyl)-1-(1-(trifluoromethyl) cyclopropanecarbonyl)pyrrolidine-2-carboxamide;

(2S,4R)—N-(1-cyanocyclopropyl)-4-(2-methyl-4-(1-methyl-3-(trifluoromethyl)-1H-pyrazol-5-yl)phenylsulfonyl)-1-(1-(trifluoromethyl)cyclopropanecarbonyl) pyrrolidine-2-carboxamide;

(2S,4R)—N-(1-cyanocyclopropyl)-4-(4-(3,5-dimethyl-1H-1,2,4-triazol-1-yl)phenyl sulfonyl)-1-(1-(trifluoromethyl)cyclopropanecarbonyl)pyrrolidine-2-carboxamide;

(2S,4R)-4-(4-(1H-1,2,3-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(4-(3-(trifluoromethyl)-1H-pyrazol-1-yl)phenyl sulfonyl)-1-(1-(trifluoromethyl)cyclopropanecarbonyl)pyrrolidine-2-carboxamide;

(2S,4R)—N-(1-cyanocyclopropyl)-4-(4-(5-methyl-3-(trifluoromethyl)-1H-pyrazol-1-yl)phenyl sulfonyl)-1-(1-(trifluoromethyl)cyclopropanecarbonyl)pyrrolidine-2-carboxamide;

(2S,4R)—N-(1-cyanocyclopropyl)-4-(2'-formylbiphenyl-4-ylsulfonyl)-1-(1-(trifluoromethyl)cyclopropanecarbonyl)pyrrolidine-2-carboxamide;

(2S,4R)—N-(1-cyanocyclopropyl)-4-(2'-ethoxybiphenyl-4-ylsulfonyl)-1-(1-(trifluoromethyl)cyclopropanecarbonyl)pyrrolidine-2-carboxamide;

(2S,4R)-4-(4-(2-aminopyrimidin-5-yl)phenylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(2'-ethoxy-3-methyl-biphenyl-4-ylsulfonyl)-1-(1-(trifluoromethyl)cyclopropanecarbonyl)pyrrolidine-2-carboxamide;

(2S,4R)-4-(2'-cyano-3-methylbiphenyl-4-ylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(2'-ethoxy-4',5'-difluoro-3-methylbiphenyl-4-ylsulfonyl)-1-(1-(trifluoromethyl)cyclopropanecarbonyl)pyrrolidine-2-carboxamide;

(2S,4R)—N-(1-cyanocyclopropyl)-4-(2'-(hydroxymethyl)biphenyl-4-ylsulfonyl)-1-(1-(trifluoromethyl)cyclopropanecarbonyl)pyrrolidine-2-carboxamide;

(2S,4R)-4-(4-(2-aminopyrimidin-5-yl)-2-methylphenylsulfonyl)-N-(1-cyanocyclopropyl)-1-(1-(trifluoromethyl)cyclopropanecarbonyl)pyrrolidine-2-carboxamide;

(2S,4R)-4-[4-(2,2-Difluoro-benzo[1,3]dioxol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-1-(1-Trifluoromethyl-cyclopropanecarbonyl)-4-[2-trifluoromethyl-4-(4-trifluoromethyl-pyrazol-1-yl)-benzenesulfonyl]-pyrrolidine-2-carboxylic acid (1-cyano-cyclopropyl)-amide;

(2S,4R)-4-[4-(5-Methyl-tetrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(2,4-Dimethyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(2,4-dimethylthiazol-5-yl)phenylsulfonyl)-1-(1-(trifluoromethyl)cyclopropanecarbonyl)pyrrolidine-2-carboxamide;

(2S,4R)—N-(1-cyanocyclopropyl)-4-(4-(2-methylthiazol-5-yl)phenylsulfonyl)-1-(1-(trifluoromethyl)cyclopropanecarbonyl)pyrrolidine-2-carboxamide;

(2S,4R)—N-(1-cyanocyclopropyl)-4-(4-(2-methoxypyrimidin-5-yl)phenylsulfonyl)-1-(1-(trifluoromethyl)cyclopropanecarbonyl)pyrrolidine-2-carboxamide;

(2S,4R)-4-(2-chloro-4-(5-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(4-[1,2,3]Triazol-2-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(4-[1,2,3]Triazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(3,5-dimethylisoxazol-4-yl)phenylsulfonyl)-1-(1-(trifluoromethyl)cyclopropanecarbonyl)pyrrolidine-2-carboxamide;

(2S,4R)-4-[4-(1-Difluoromethyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(5-Methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-1-(1-Trifluoromethyl-cyclopropanecarbonyl)-4-[2-trifluoromethyl-4-(3-trifluoromethyl-1H-pyrazol-4-yl)-benzenesulfonyl]-pyrrolidine-2-carboxylic acid (1-cyano-cyclopropyl)-amide;

(2S,4R)—N-(1-cyanocyclopropyl)-4-(2'-(hydroxymethyl)-3-methylbiphenyl-4-ylsulfonyl)-1-(1-(trifluoromethyl)cyclopropanecarbonyl)pyrrolidine-2-carboxamide;

(2S,4R)—N-(1-cyanocyclopropyl)-4-(4-(2,4-dimethylthiazol-5-yl)-2-methylphenylsulfonyl)-1-(1-(trifluoromethyl)cyclopropanecarbonyl)pyrrolidine-2-carboxamide;

(2S,4R)—N-(1-cyanocyclopropyl)-4-(2-methyl-4-(2-methylthiazol-5-yl)phenyl sulfonyl)-1-(1-(trifluoromethyl)cyclopropanecarbonyl)pyrrolidine-2-carboxamide;

(2S,4R)—N-(1-cyanocyclopropyl)-4-(4-(2-methoxypyrimidin-5-yl)-2-methylphenylsulfonyl)-1-(1-(trifluoromethyl)cyclopropanecarbonyl)pyrrolidine-2-carboxamide;

(2S,4R)-4-[4-(2-Methyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(3,5-dimethylisoxazol-4-yl)-2-methylphenylsulfonyl)-1-(1-(trifluoromethyl)cyclopropanecarbonyl)pyrrolidine-2-carboxamide;

(2S,4R)-4-(4-Tetrazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(4-(3-chloro-1H-1,2,4-triazol-1-yl)-2-methylphenylsulfonyl)-N-(1-cyanocyclopropyl)-1-(1-(trifluoromethyl)cyclopropanecarbonyl)pyrrolidine-2-carboxamide;

(2R,4R)-4-(4-(3-chloro-1H-1,2,4-triazol-1-yl)-2-methylphenylsulfonyl)-N-(1-cyanocyclopropyl)-1-(1-(trifluoromethyl)cyclopropanecarbonyl)pyrrolidine-2-carboxamide;

(2S,4R)-4-[4-(1-Methyl-3-trifluoromethyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide; and (2S,4R)-4-(4-(3-chloro-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide.

The invention particularly relates to a compound of formula (I) selected from:

(2S,4R)-4-[4-(2-Methyl-5-trifluoromethyl-2H-pyrazol-3-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-(2-chloro-4-(5-methyl-2H-tetrazol-2-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(5-methyl-1H-tetrazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(2H-1,2,3-triazol-2-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(1H-1,2,3-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3,5-dimethyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3-chloro-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(3-(trifluoromethyl)-1H-pyrazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(2-chloro-4-(5-methyl-3-(trifluoromethyl)-1H-pyrazol-1-yl)phenylsulfonyl)-N-(1-cyanocyclopropyl)-1-(1-(trifluoromethyl) cyclopropanecarbonyl)pyrrolidine-2-carboxamide;

(2S,4R)—N-(1-cyanocyclopropyl)-4-(2-methyl-4-(3-(trifluoromethyl)-1H-pyrazol-1-yl)phenylsulfonyl)-1-(1-(trifluoromethyl)cyclopropanecarbonyl)pyrrolidine-2-carboxamide;

(2S,4R)-4-[4-(5-Methyl-3-trifluoromethyl-pyrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(3-Methyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(3-Methyl-[1,2,4]triazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-(4-(1H-1,2,4-triazol-1-yl)-2-(trifluoromethyl)phenylsulfonyl)-N-(1-cyanocyclopropyl)-1-(1-(trifluoromethyl)cyclopropanecarbonyl)pyrrolidine-2-carboxamide;

(2S,4R)-4-[4-(3,5-Dimethyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(3-Chloro-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(5-methyl-1H-1,2,4-triazol-1-yl)-2-(trifluoromethyl)phenyl sulfonyl)-1-(1-(trifluoromethyl)cyclopropanecarbonyl) pyrrolidine-2-carboxamide;

(2S,4R)—N-(1-cyanocyclopropyl)-4-(2-methyl-4-(1-methyl-3-(trifluoromethyl)-1H-pyrazol-5-yl)phenylsulfonyl)-1-(1-(trifluoromethyl)cyclopropanecarbonyl) pyrrolidine-2-carboxamide;

(2S,4R)-1-(1-Trifluoromethyl-cyclopropanecarbonyl)-4-[2-trifluoromethyl-4-(4-trifluoromethyl-pyrazol-1-yl)-benzenesulfonyl]-pyrrolidine-2-carboxylic acid (1-cyano-cyclopropyl)-amide;

(2S,4R)-4-[4-(5-Methyl-tetrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(2,4-Dimethyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-(2-chloro-4-(5-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(4-[1,2,3]Triazol-2-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(4-[1,2,3]Triazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-[4-(1-Difluoromethyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(5-Methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-1-(1-Trifluoromethyl-cyclopropanecarbonyl)-4-[2-trifluoromethyl-4-(3-trifluoromethyl-1H-pyrazol-4-yl)-benzenesulfonyl]-pyrrolidine-2-carboxylic acid (1-cyano-cyclopropyl)-amide;

(2S,4R)—N-(1-cyanocyclopropyl)-4-(4-(2,4-dimethylthiazol-5-yl)-2-methylphenylsulfonyl)-1-(1-(trifluoromethyl)cyclopropanecarbonyl)pyrrolidine-2-carboxamide;

(2S,4R)—N-(1-cyanocyclopropyl)-4-(2-methyl-4-(2-methylthiazol-5-yl)phenyl sulfonyl)-1-(1-(trifluoromethyl)cyclopropanecarbonyl)pyrrolidine-2-carboxamide;

(2S,4R)-4-[4-(2-Methyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(3,5-dimethylisoxazol-4-yl)-2-methylphenylsulfonyl)-1-(1-(trifluoromethyl)cyclopropanecarbonyl)pyrrolidine-2-carboxamide;

(2S,4R)-4-(4-Tetrazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(4-(3-chloro-1H-1,2,4-triazol-1-yl)-2-methylphenylsulfonyl)-N-(1-cyanocyclopropyl)-1-(1-(trifluoromethyl)cyclopropanecarbonyl)pyrrolidine-2-carboxamide;

(2R,4R)-4-(4-(3-chloro-1H-1,2,4-triazol-1-yl)-2-methylphenylsulfonyl)-N-(1-cyanocyclopropyl)-1-(1-(trifluoromethyl)cyclopropanecarbonyl)pyrrolidine-2-carboxamide; and (2S,4R)-4-[4-(1-Methyl-3-trifluoromethyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide.

The invention particularly relates to a compound of formula (I) which is (2S,4R)-4-[4-(5-Methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide.

The following abbreviations are used in the present application:
AcOEt: Ethyl acetate;
ACN: Acetonitrile;
boc: tert-Butyloxycarbonyl
BOP: Benzotriazolyl-N-oxy-tris(dimethylamino)-phosphonium hexafluorophosphate;
BOP-Cl: Bis-(2-oxo-3-oxazolidinyl)-phosphinic acid chloride;
Cbz: Carbobenzyloxy
CDI: 1,1'-Carbonyldiimidazole;
DCM: Dichloromethane;
DIEA: Diisopropyl ethyl amine;
DMAP: 4-Dimethylaminopyridine;
DMF: N,N-Dimethylformamide;
EDCI: N-(3-Dimethylaminopropyl)-N'-ethyl-carbodiimide hydrochloride;
EtOAc: Ethyl acetate;
Fmoc: 9-Fluorenylmethyloxycarbonyl
h: hour;
HATU: O-(7-azabenzotriazol-1-yl)-1,1,3,3-tetramethyluronium hexafluorophosphate;
HOBT: 1-Hydroxybenzotriazole;
Hunig's Base: Ethyl-diisopropyl-amine;
mCPBA or MCPBA: meta-Chloroperoxybenzoic acid;
MeOH: Methanol;
Mes-Cl: Mesyl chloride;
min: minute;
$Na_2SO_4$: Sodium sulfate;
Nos-Cl: 3-Nitrobenzenesulfonyl chloride;
$Pd_2(dba)_3$: Tris(dibenzylideneacetone)dipalladium;
PyBOP: Benzotriazol-1-yl-oxytripyrrolidinephosphonium hexafluorophosphate;
TBTU: O-(Benzotriazol-1-yl)-N,N,N',N'-tetramethyluronium terafluoroborate;
THF: Tetrahydrofurane;
TFA: Trifluoroacetic acid; and
Tos-Cl: Toluene-4-sulfonyl chloride.

The compound of formula (I) can be manufacture by known procedures or according to the procedures described in schemes 1 and 2 below.

Scheme 1

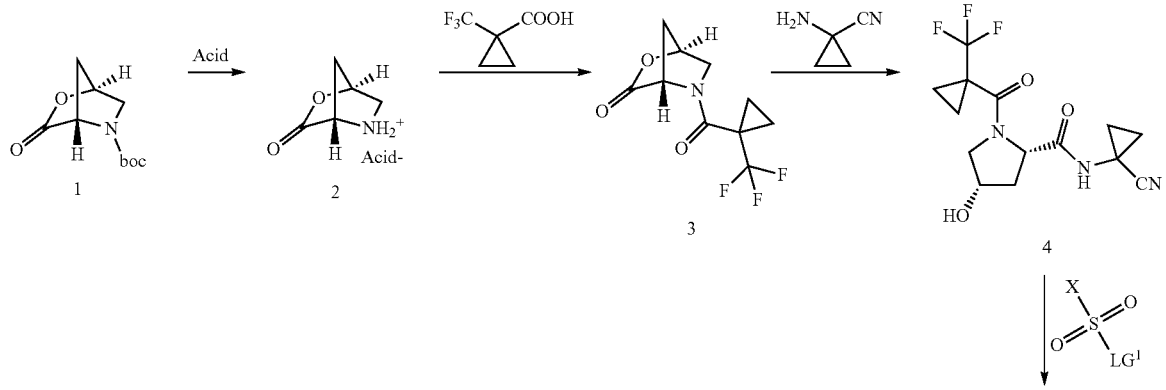

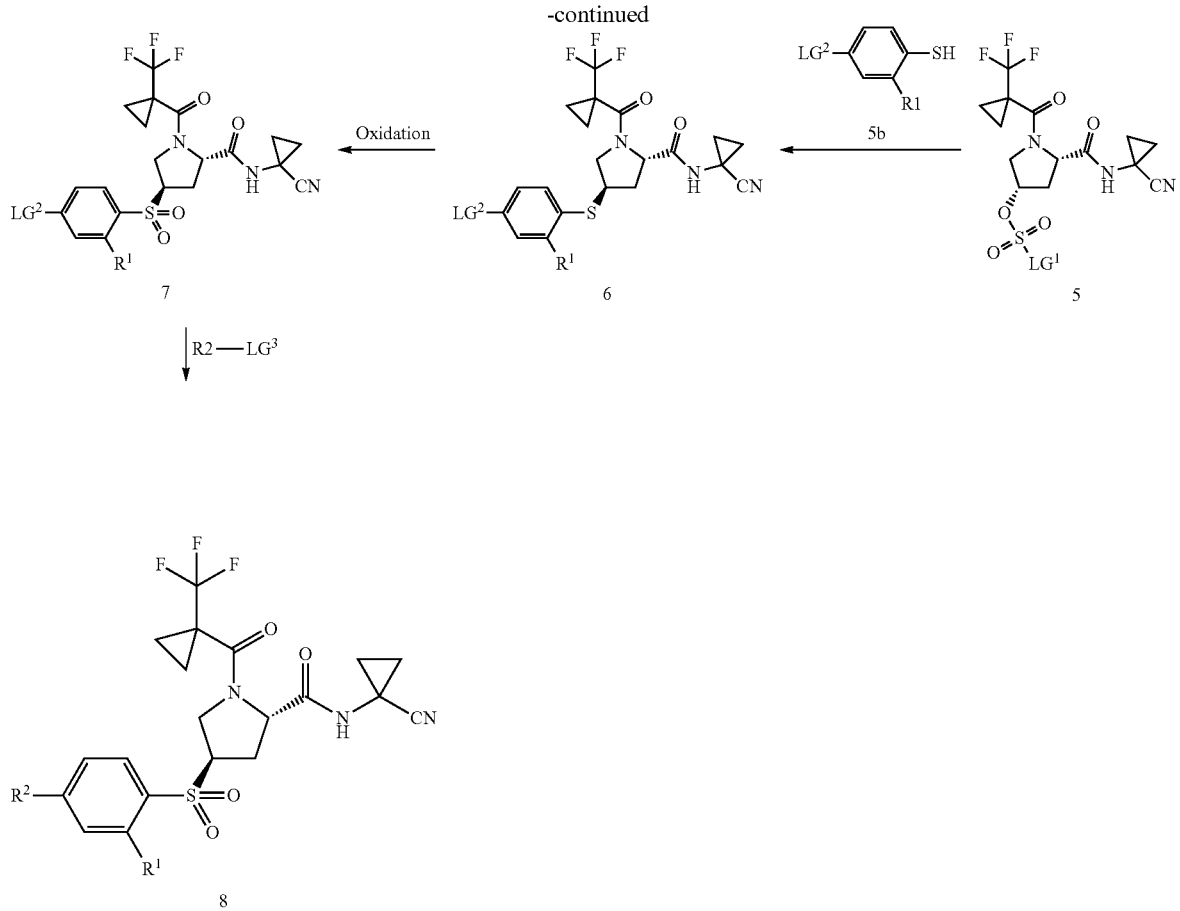

Definitions: a) Acid: e.g. methane sulfonic acid, phenyl sulfonic acid, trifluoromethyl sulfonic acid, HCl, HBr, sulfuric acid, TFA, formic acid; b) X: OH, Cl, O—SO$_2$—LG$^1$; c) LG$^1$: Leaving group such as phenyl, methyl, ethyl, 3-nitrophenyl, 4-methylphenyl, 4-bromophenyl, trifluoromethyl; d) LG$^2$: F, Cl, Br, I, B(OH)$_2$, B(OR$^3$)$_2$; e) R$^1$ as defined above; f) R$^3$: Methyl, ethyl or both R$^3$ form together with the oxygen and boron atoms to which they are attached a ring such as 4,4,5,5-tetramethyl-[1,3,2]dioxaborolane; g) Oxidation: oxidation is performed with one of the oxidizing agents known in the art such as hydrogen peroxide or metal complexes of hydrogen peroxide, oxone or mCPBA; h) R$^2$ as defined above; i) LG$^3$: H, B(OH)$_2$, B(OR$^3$)$_2$, Br or I.

Boc-protected compound 1 is deprotected with an appropriate acid such as TFA, HCl, formic acid, sulfuric acid etc. to yield after crystallization the salt 2. Reaction of salt 2 with 1-trifluoromethyl-cyclopropanecarboxylic acid in the presence of a base such as triethyl amine, Hunig's Base or N-methyl morpholine and an appropriate amide coupling reagent such as HATU, PyBop, TBTU, CDI, EDCI, BOP or Bop-Cl yields amide 3. Alternatively, 2 is reacted with 1-trifluoromethyl-cyclopropanecarboxylic acid in the presence of e.g. oxalyl chloride, thionyl chloride, phosphoryl chloride, phosgene or triphosgene to yield amide 3. Ring opening of the lactam 3 with 1-amino-cyclopropanecarbonitrile or salts therefore, e.g. hydrochloride salt, is accommodated in the presence of an appropriate base such as e.g. Hunig's base, triethyl amine, sodium 2-ethylhexanoate, pyridine or lutidine at elevated temperature between 30° C.-80° C. to yield alcohol 4. Reaction of alcohol 4 with a sulfonylchloride derivative such as methane sulfonylchloride, phenyl sulfonylchloride, tosylchloride, nosylchloride, brosylchloride or anhydrides such as triflic anhydride yields compound 5. Thioether 6 is obtained by reaction of sulfonate 5 with thiophenol 5b in the presence of an appropriate base such as Hunig's base, triethyl amine, pyridine, lutidine, Na$_2$CO$_3$, K$_2$CO$_3$ or Cs$_2$CO$_3$. Subsequent oxidation of thioether 6 with a peroxide source such as hydrogen peroxide, mCPBA, oxone or metal complexes of hydrogen peroxide such as MoO$_2$Cl$_2$/H$_2$O$_2$ or Na$_x$W$_y$O$_z$/H$_2$O$_2$ systems yields sulfone 7. Compound 7 can be either directly reacted with heterocyclic compounds in a S$_N$Ar fashion in the presence of a base such as Hunig's base, triethyl amine, pyridine, lutidine, Na$_2$CO$_3$, K$_2$CO$_3$ or Cs$_2$CO$_3$ or via a Suzuki reaction with boronic acids or esters thereof using metal catalysts and bases known in the art such as e.g. Pd(PPh$_3$)$_4$, Pd$_2$(dba)$_3$ or a Pd-source with a phosphine ligand to yield the final compounds 8.

Scheme 2

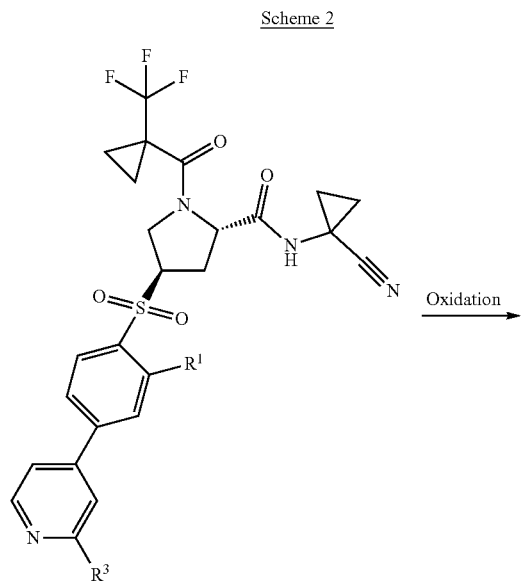

Definitions: a) $R^1$ as defined above; b) $R^3$: methyl, chloro.

Oxidation of pyridine derivatives to the corresponding N-oxide can be accomplished by using an oxidation reagent such as hydrogen peroxide, mCPBA or oxone.

The invention thus also relates to a process for the manufacture of a compound of formula (I) comprising:

(a) The reaction of a compound of formula (A)

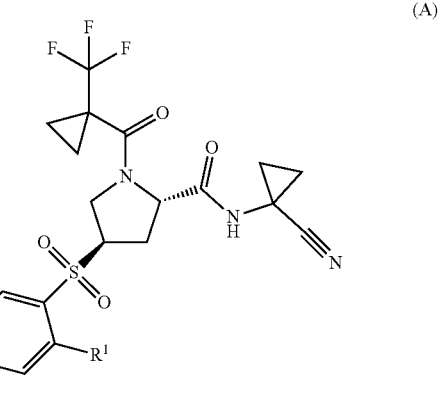

in the presence of a compound of formula R2-$LG^2$ wherein $R^1$ and R2 are as defined in any one of claims 1 to 6 and wherein $LG^1$ is F, Cl, Br, I, $B(OH)_2$ or $B(OR^3)_2$, $LG^2$ is H, $B(OH)_2$, $B(OR^3)_2$, Br or I and each $R^3$ is independently selected from methyl, ethyl and both $R^3$ together with the oxygen and boron atoms to which they are attached form an organoboron ring; or (b) The reaction of a compound of formula (B)

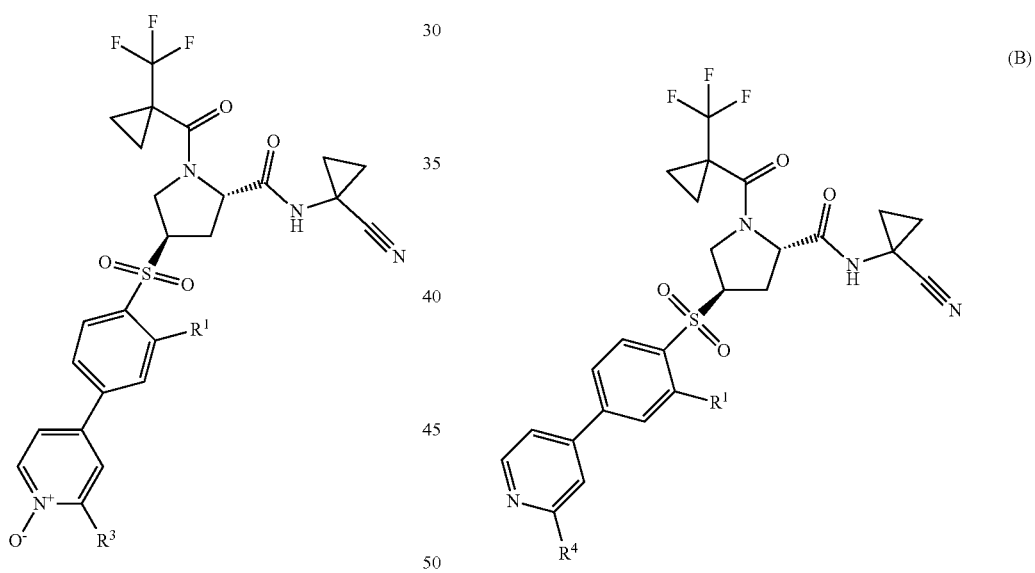

in the presence of an oxidation reagent, wherein $R^1$ is as defined in any one of claims 1 to 6 and $R^4$ is halogen or alkyl.

Examples of oxidation reagents are e.g. hydrogen peroxide, mCPBA or oxone.

4,4,5,5-tetramethyl-1,3,2-dioxaborolane is an example of organoboron ring.

The invention further relates to a compound of formula (I) when manufactured according to the above process.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. The compounds of the invention may be administered in particular by intravitreal administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention thus also relates to:

A compound of formula (I) for use as therapeutically active substance;

A pharmaceutical composition comprising a compound of formula (I) and a therapeutically inert carrier;

The use of a compound of formula (I) for the preparation of medicaments for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration;

A compound of formula (I) for use in the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration; and A method for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration, which method comprises administering an effective amount of a compound of formula (I) to a patient in need thereof.

The invention will now be illustrated by the following examples which have no limiting character.

EXAMPLES

Example 1

(2S,4R)-4-[4-(2-Chloro-1-oxy-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

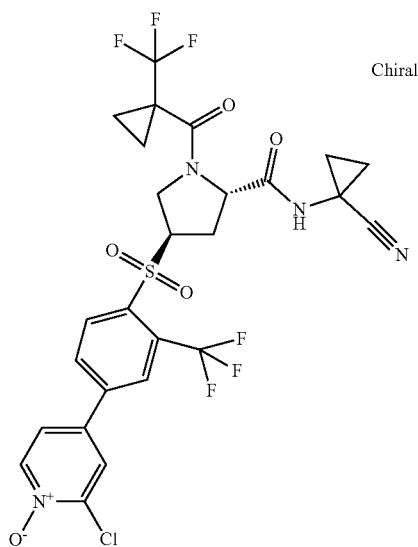 [SMILES: N#CC1(NC(=O)[C@@H]2C[C@@H](S(=O)(=O)c3ccc(-c4cc[n+]([O-])c(Cl)c4)cc3C(F)(F)F)CN2C(=O)C2(C(F)(F)F)CC2)CC1]

In a 10 mL round-bottomed flask CAS 1252637-43-6 (0.05 g, 78.7 µmol, Eq: 1.00) was combined with dichloromethane (1 mL) to give a colorless solution. 3-Chlorobenzoperoxoic acid (20.4 mg, 118 µmol, Eq: 3×1.5 each after 24 h, 48 h, 72 h) was added. The reaction mixture was heated to 22° C. and stirred for totally 168 h. The crude material was purified by preparative HPLC to yield the title compound as a colorless amorphous solid (25 mg; 50%). m/z=651.2 [M+H]$^+$.

Example 2

(2S,4R)-4-[4-(2-Methyl-1-oxy-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

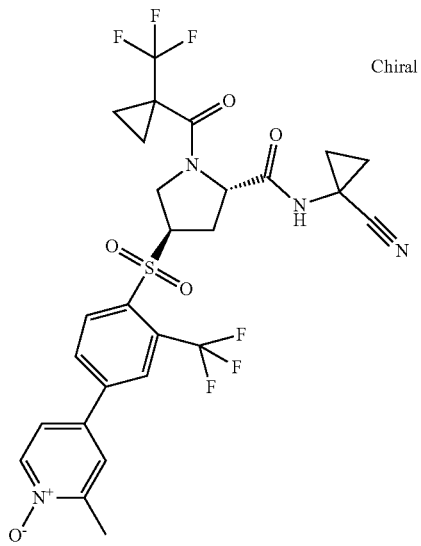 [SMILES: Cc1cc(-c2ccc(S(=O)(=O)[C@@H]3C[C@@H](C(=O)NC4(C#N)CC4)N(C(=O)C4(C(F)(F)F)CC4)C3)c(C(F)(F)F)c2)cc[n+]1[O-]]

In a 10 mL round-bottomed flask, CAS 1252637-46-9 (50 mg, 81.4 μmol, Eq: 1.00) was combined with dichloromethane (1 mL) to give a colorless solution. mCPBA (21.1 mg, 122 μmol, Eq: 1.5) was added. The reaction mixture was heated to 22° C. and stirred for totally 20 h. The crude material was purified by preparative HPLC to yield the title compound as a colorless amorphous solid (40 mg; 78%). m/z=631.3 [M+H]$^+$.

Example 3

(2S,4R)-4-[4-(2-Methyl-5-trifluoromethyl-2Hpyrazol-3-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

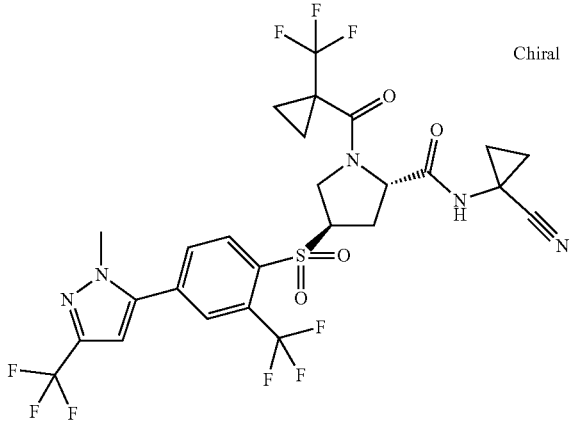 [SMILES: Cn1nc(C(F)(F)F)cc1-c1ccc(S(=O)(=O)[C@@H]2C[C@@H](C(=O)NC3(C#N)CC3)N(C(=O)C3(C(F)(F)F)CC3)C2)c(C(F)(F)F)c1]

a) (1S,4S)-3-Oxo-2-oxa-5-azonia-bicyclo[2.2.1]heptane methanesulfonate

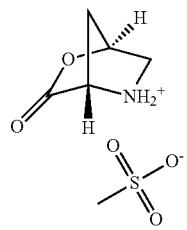

(1S,4S)-3-Oxo-2-oxa-5-aza-bicyclo[2.2.1]heptane-5-carboxylic acid tert-butyl ester (100.0 g, 469 mmol) was dissolved in ethyl acetate (970 mL) and methanesulfonic acid (43.5 mL, 659 mmol) was added at 45° C. The mixture was stirred for 16 h at 45° C. The suspension was cooled to room temperature, filtered, and the precipitate was washed with ethyl acetate (240 mL) and dried in vacuo to yield the title compound as a white crystalline solid (94.2 g, 96%). m/z=113 [M−H]$^−$.

b) (1S,4S)-5-(1-Trifluoromethyl-cyclopropanecarbonyl)-2-oxa-5-aza-bicyclo[2.2.1]heptan-3-one

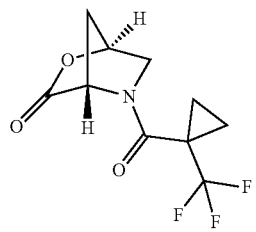 [SMILES: O=C1O[C@H]2C[C@@H]1N(C(=O)C1(C(F)(F)F)CC1)C2]

1-Trifluoromethyl-cyclopropanecarboxylic acid (167.0 g, 1084 mmol) was suspended in toluene (500 mL) and then dimethylformamide (3.6 mL, 47 mmol) was added. The mixture was cooled to 2° C. (ice bath) and a solution of oxalyl chloride (90 mL, 1037 mmol) in toluene (167 mL) was added dropwise (within 25 min). The mixture was then stirred for additional 30 min, followed by 4 h at room temperature. Subsequently, it was cooled to 0° C. again (dry ice/methanol bath) and (1S,4S)-3-oxo-2-oxa-5-azonia-bicyclo[2.2.1]heptane methanesulfonate (200 g, 956 mmol), tetrahydrofuran (330 mL) and triethylamine (500 mL, 3.59 mol) were slowly added, keeping the reaction temperature below 5° C. Especially after addition of 50% of triethylamine, the reaction becomes strongly exothermic and efficient cooling is essential. The mixture was stirred for 20 h at room temperature, before it was poured onto an aqueous citric acid solution (10% in water, 1.6 L) and the phases were separated. The aqueous phase was extracted with ethyl acetate (3×500 mL). The combined organic extracts were washed with 20 brine (500 mL), dried over sodium sulfate, and concentrated in vacuo. The crude product (245 g, brown oil) was dissolved in dichloromethane (330 mL) before ethyl acetate (130 mL) and heptane (660 mL) were added and dichloromethane was carefully distilled off in vacuo. The product started to crystallize. The suspension was cooled to 2° C. (ice bath) and stirred for 1 h, before it was filtered. The precipitate was washed with ethyl acetate/heptane 1:9 (v/v, 300 mL) and dried in vacuo to afford the title compound as a light brown powder (219 g, 92%). $^1$H NMR (CDCl3, 400 MHz): d 1.17-1.25 (m, 1H), 1.30 (dd, J=5.3 Hz, 8.3 Hz, 1H), 1.37-1.46 (m, 2H), 2.13 and 2.37 (AB, J$_{AB}$=10.7 Hz, each 1H), 3.63 and 3.73 (AB, J$_{AB}$=12.1 Hz, each 1H), 4.99 (s, 1H), 5.21 (s, 1H).

c) (2S,4S)-4-Hydroxy-1-(1-trifluoromethyl-cyclopropanecarbonyl)-pyrrolidine-2-carboxylic acid (1-cyano-cyclopropyl)-amide

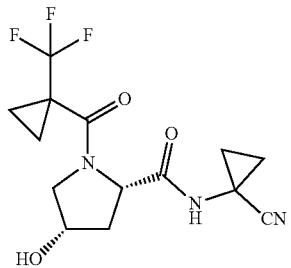 [SMILES: N#CC1(NC(=O)[C@@H]2C[C@H](O)CN2C(=O)C2(C(F)(F)F)CC2)CC1]

(1S,4S)-5-(1-Trifluoromethyl-cyclopropanecarbonyl)-2-oxa-5-aza-bicyclo[2.2.1]heptan-3-one (220 g, 883 mmol), 1-amino-cyclopropanecarbonitrile hydrochloride (140 g, 1.18 mol) and sodium 2-ethylhexanoate (97%, 230 g, 1.34 mol) were dissolved in water (1.32 L). The mixture was stirred for 20 h at 53° C. After cooling to room temperature, tetrahydrofuran (880 mL) was added and the mixture was acidified by addition of concentrated hydrochloric acid (37% m/m, 47 mL), followed by the addition of sodium chloride (440 g). After extraction with ethyl acetate (1×1.4 L, 3×550 mL), the combined organic extracts were dried over sodium sulfate and concentrated in vacuo. At a volume of ca. 1.5 L, the product started to crystallize upon addition of seed crystals. The volume of the suspension was further reduced to ca. 500 mL and cooled to 2° C. (ice bath). After stirring for 60 min, the crystals were filtered off, washed with ethyl acetate/heptane 1:1 (v/v, 600 mL) and heptane (300 mL), and dried in vacuo to provide the title compound as off-white crystals (255.0 g, 87%). $^1$H NMR (CDCl3, 400 MHz):d 1.18-1.29 (m, 4H), 1.30-1.42 (m, 2H), 1.50-1.59 (m, 2H), 2.17-2.26 (m, 1H), 2.29 (d, J=14.5 Hz, 1H), 3.73 and 3.96 (ABX, JAB=11.8 Hz, JAX=4.3 Hz, JBX=0 Hz, each 1H), 4.43-4.53 (m, 2H), 4.81 (brd, J=8.3 Hz, 1H), 7.73 (s, 1H).

d) Benzenesulfonic acid (3S,5S)-5-(1-cyano-cyclopropylcarbamoyl)-1-(1-trifluoromethyl-cyclopropanecarbonyl)-pyrrolidin-3-yl ester

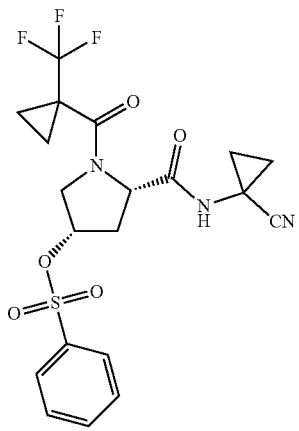 [SMILES: N#CC1(NC(=O)[C@@H]2C[C@H](OS(=O)(=O)c3ccccc3)CN2C(=O)C2(C(F)(F)F)CC2)CC1]

(2S,4S)-4-Hydroxy-1-(1-trifluoromethyl-cyclopropanecarbonyl)-pyrrolidine-2-carboxylic acid (1-cyano-cyclopropyl)-amide (100.0 g, 301.8 mmol) was dissolved in tetrahydrofuran (500 mL). The mixture was cooled to 2° C. (ice bath), benzenesulfonyl chloride (99%, 48 mL, 370.5 mmol), 4-(dimethylamino)pyridine (98%, 2.0 g, 16.0 mmol), and triethylamine (75.0 mL, 539 mmol) were added subsequently and the mixture was stirred for 15 min. The reaction was allowed to warm to room temperature and stirred for 20 h. After cooling to 2° C. (ice bath), water (150 mL) and methanol (350 mL) were added. Tetrahydrofuran was distilled off carefully in vacuo (ca. 500 mL) and water (500 mL) was added slowly. After addition of 300 mL water, crystallization was induced by addition of seed crystals. The resulting suspension was stirred for 30 min at 2° C. (ice bath) and filtered. The solid was washed with methanol/water 1:2 (v/v, 300 mL) and heptane (300 mL) and dried in vacuo to afford the title compound as off-white crystals (140.8 g, 99%). $^1$H NMR (CDCl3, 400 MHz): d 1.06-1.27 (m, 4H), 1.28-1.41 (m, 2H), 1.44-1.54 (m, 2H), 2.26 (ddd, J=5.9 Hz, 9.4 Hz, 14.2 Hz, 1H), 2.59 (ddd, J=3.8 Hz, 3.8 Hz, 14.2 Hz, 1H), 3.90 and 4.03 (ABX, JAB=12.5 Hz, JAX=4.0 Hz, JBX=5.2 Hz, each 1H), 4.57 (br d, J=5.1 Hz, 1H), 5.02-5.09 (m, 1H), 7.08 (br s, 1H), 7.61 (t, J=7.8 Hz, 2H), 7.71 (t, J=7.5 Hz, 1H), 7.95 (d, J=7.2 Hz, 2H).

e) (2S,4R)-4-(4-Bromo-2-trifluoromethyl-phenylsulfanyl)-1-(1-trifluoromethyl-cyclopropanecarbonyl)-pyrrolidine-2-carboxylic acid (1-cyano-cyclopropyl)-amide

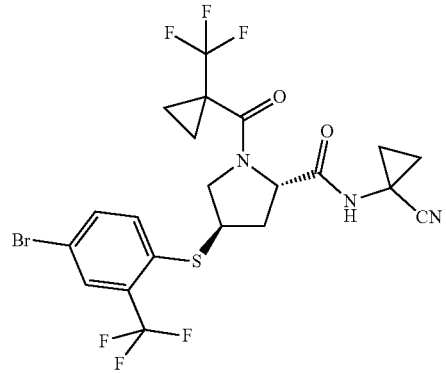 [SMILES: N#CC1(NC(=O)[C@@H]2C[C@@H](Sc3ccc(Br)cc3C(F)(F)F)CN2C(=O)C2(C(F)(F)F)CC2)CC1]

Example 3d) (7.03 g, 14.9 mmol, Eq: 1.00) was dissolved in propionitrile (80 mL) and 4-bromo-2-trifluoromethyl-benzenethiol CAS 1208075-10-8 (5.75 g, 22.4 mmol, Eq: 1.50) was added. Now, triethylamine (3.02 g, 4.16 mL, 29.8 mmol, Eq: 2.00) was carefully added and the reaction mixture was stirred at reflux for 18 h. The reaction mixture was extracted with 10% aqueous Na$_2$CO$_3$ solution/AcOEt. The organic layers were dried over Na$_2$SO$_4$, filtered and evoporated. The crude material was purified by flash chromatography (silica gel, 120 g, 0% to 50% EtOAc in heptane) to yield the title compound as a white foam (8.14 g; 96%). m/z=571.9/570.1 [M+H]$^+$. (Br isotopes)

f) (2S,4R)-4-(4-Bromo-2-trifluoromethyl-benzene-sulfonyl-1-(1-trifluoromethyl-cyclopropanecarbonyl)-pyrrolidine-2-carboxylic acid (1-cyano-cyclopropyl)-amide

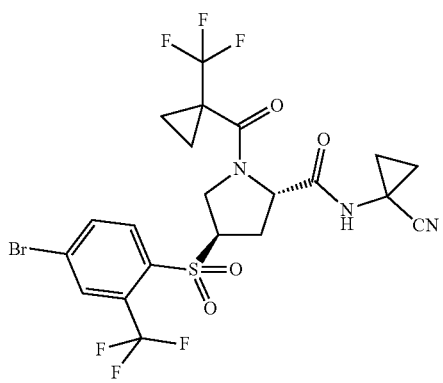 [SMILES: N#CC1(NC(=O)[C@@H]2C[C@@H](S(=O)(=O)c3ccc(Br)cc3C(F)(F)F)CN2C(=O)C2(C(F)(F)F)CC2)CC1]

Example 3e) (8.14 g, 14.3 mmol, Eq: 1.00) was dissolved in dichloromethane (50 mL) and mCPBA (5.17 g, 30.0 mmol, Eq: 2.10) was carefully added portionwise. The reaction mixture was stirred over night at 25° C. The reaction mixture was extracted with 10% aqueous $Na_2CO_3$ solution and aqueous $Na_2S_2O_3$ saturated solution. The organic layers were dried over $Na_2SO_4$ and $Na_2SO_3$ for 2 h, filtered and evaporated (attention peroxide!) to yield the title compound as a white foam (8.6 g; 100%). m/z=602.0/604.0 $[M+H]^+$. (Br isotopes)

g) (2S,4R)-4-[4-(2-Methyl-5-trifluoromethyl-2Hpyrazol-3-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

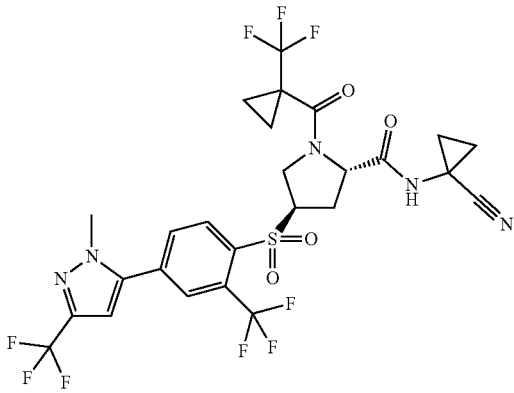

Example 3f) (500 mg, 830 µmol, Eq: 1.00), 1-methyl-5-(4,4,5,5-tetramethyl-1,3,2-dioxaborolan-2-yl)-3-(trifluoromethyl)-1H-pyrazole (275 mg, 996 µmol, Eq: 1.20) and triphenylphosphine (43.5 mg, 166 µmol, Eq: 0.20) were dissolved in 1,2-dimethoxyethane (6 mL). $Pd(OAc)_2$ (18.6 mg, 83.0 µmol, Eq: 0.10) and 2M aqueous $Na_2CO_3$ solution (1.5 mL) were added to the solution. The reaction mixture was stirred at 60° C. for 8 h. The reaction mixture was poured into 0.1 M aqueous HCl solution (100 mL) and extracted with DCM. The aqueous layer was washed with DCM (3×50 mL). The organic layers were dried over $Na_2SO_4$ and concentrated in vacuo. The crude material was purified by flash chromatography (silica gel, 20 g, 0% to 80% EtOAc in heptane) to yield the title compound as light yellow foam (410 mg; 74%). m/z=670.1169 $[M-H]^-$.

Example 4

(2S,4R)-4-(2'-Trifluoromethoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide

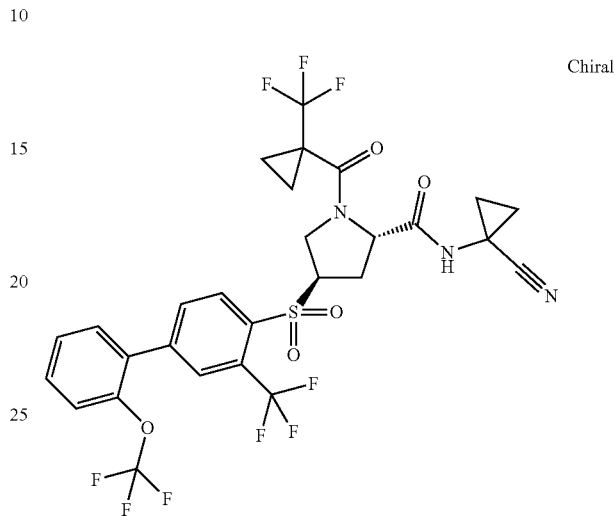

Example 3f) (50 mg, 83.0 µmol, Eq: 1.00), 2-(trifluoromethoxy)phenylboronic acid (20.5 mg, 99.6 µmol, Eq: 1.20) and triphenylphosphine (4.35 mg, 16.6 µmol, Eq: 0.20) were dissolved in 1,2-dimethoxyethane (1 mL). $Pd(OAc)_2$ (1.86 mg, 8.3 µmol, Eq: 0.10) and aqueous 2M $Na_2CO_3$ solution (250 µl) were added to the solution and stirred at 50° C. for 8 h. The crude material was filtered and purified by preparative HPLC to yield the title compound as a white solid (41 mg; 72%). m/z=684.0 $[M+H]^+$.

Example 5

(2S,4R)-4-(2'-Ethoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide

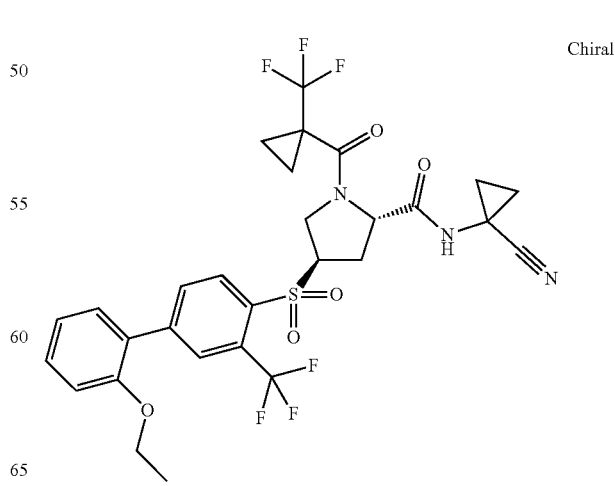

Example 5 was prepared in analogy to example 4 starting from example 3f) and 2-ethoxyphenylboronic acid to yield the title compound as a white solid (40 mg; 75%). m/z=644.1 [M+H]$^+$.

Example 6

(2S,4R)-4-(2'-Cyclopropoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide

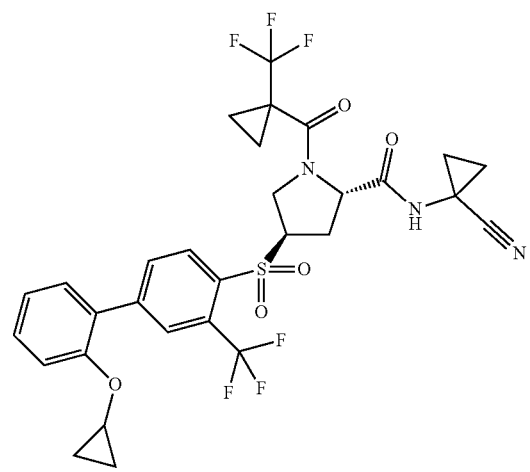

Chiral

Example 6 was prepared in analogy to example 4 starting from example 3f) and 2-cyclopropoxyphenylboronic acid to yield the title compound as a white solid (39 mg; 72%). m/z=656.3 [M+H]$^+$.

Example 7

(2S,4R)-4-(4-Cyclobutoxy-2-trifluoromethyl-benzenesulfonyl)-1-(1-trifluoromethyl-cyclopropanecarbonyl)-pyrrolidine-2-carboxylic acid (1-cyano-cyclopropyl)-amide

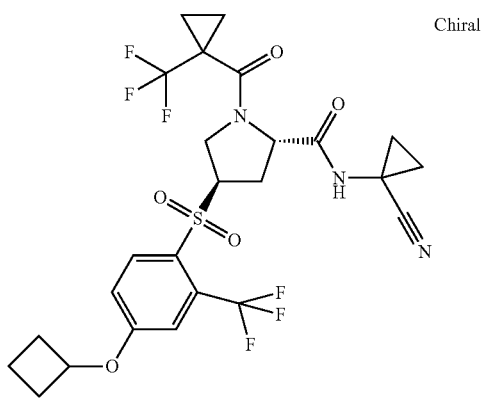 [SMILES: N#CC1(NC(=O)[C@@H]2C[C@@H](S(=O)(=O)c3ccc(OC4CCC4)cc3C(F)(F)F)CN2C(=O)C2(C(F)(F)F)CC2)CC1]

Chiral a) (2S,4R)-4-(4-Fluoro-2-trifluoromethyl-phenylsulfanyl)-1-(1-trifluoromethyl-cyclopropanecarbonyl)-pyrrolidine-2-carboxylic acid (1-cyano-cyclopropyl)-amide

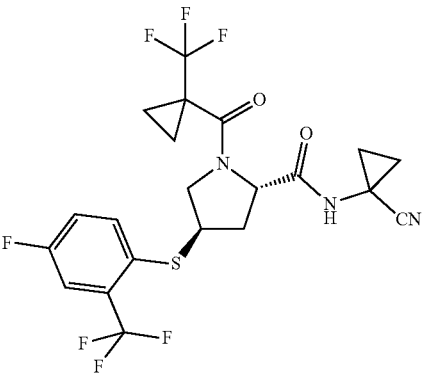 [SMILES: N#CC1(NC(=O)[C@@H]2C[C@@H](Sc3ccc(F)cc3C(F)(F)F)CN2C(=O)C2(C(F)(F)F)CC2)CC1]

In a 250 mL four-necked flask, example 3d) (7 g, 14.8 mmol, Eq: 1.00) and 4-fluoro-2-trifluoromethyl-benzenethiol (CAS 1208077-00-2) (4.08 g, 20.8 mmol, Eq: 1.40) were combined with propionitrile (70 mL) to give a yellow solution. Triethylamine (5.38 mL, Eq: 2.60) was added at 22° C. The reaction mixture was heated to 110° C. and stirred for 3 h. The reaction mixture was poured into ethylacetate (300 mL) and extracted with aqueous 10% Na$_2$CO$_3$ solution (2×100 mL). The aqueous layer was back-extracted with EtOAc (2×250 mL). The organic layers were combined, washed with saturated aqueous NaCl solution (1×75 mL). The organic layers were dried over Na$_2$SO$_4$ and concentrated in vacuo. The crude material was purified by flash chromatography (silica gel, 120 g, 20% to 70% EtOAc in heptane) to yield the title compound as a colorless foam (6.83 g; 90%). m/z=510.0 [M+H]$^+$.

b) (2S,4R)-4-(4-Fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide

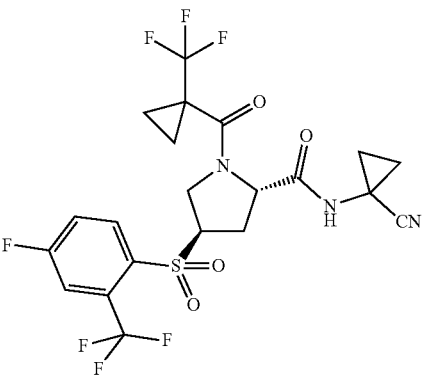 [SMILES: N#CC1(NC(=O)[C@@H]2C[C@@H](S(=O)(=O)c3ccc(F)cc3C(F)(F)F)CN2C(=O)C2(C(F)(F)F)CC2)CC1]

In a 250 mL round-bottomed flask, example 7a) (5.85 g, 11.5 mmol, Eq: 1.00) was combined with dichloromethane (80 mL) to give a white suspension. 3-chloroperoxybenzoic acid (5.15 g, 29.9 mmol, Eq: 2.60) was added. The reaction mixture was stirred for 48 h at 22° C. After that, 3-chloroperoxybenzoic acid (991 mg, 5.74 mmol, Eq: 0.5) was added and the reaction mixture was stirred for additional 72 h. The reaction mixture was poured into 200 mL dichloromethane and extracted with aqueous 10% Na$_2$CO$_3$ solution (3×150 mL). The aqueous layer was back-extracted with dichloromethane (3×150 mL). The organic layers were combined, washed with saturated aqueous Na$_2$S$_2$O$_3$-solution (4×100 mL)→(Peroxide Test), brine (1×100 mL), dried over Na$_2$SO$_4$ and concentrated in vacuo to yield the title compound as a white solid (6.36 g; 100%). m/z=542.3 [M+H]$^+$. m/z=540.3 [M−H]$^−$.

c) (2S,4R)-4-(4-Cyclobutoxy-2-trifluoromethyl-benzenesulfonyl)-1-(1-trifluoromethyl-cyclopropanecarbonyl)-pyrrolidine-2-carboxylic acid (1-cyano-cyclopropyl)-amide

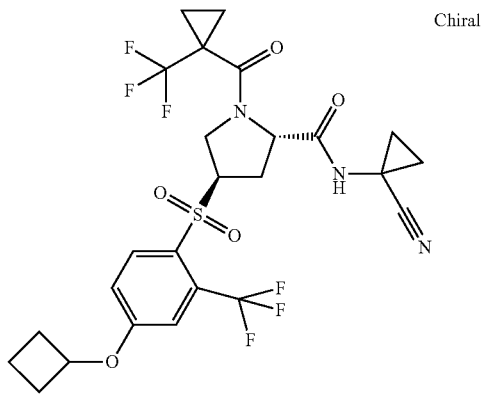 [SMILES: N#CC1(NC(=O)[C@@H]2C[C@@H](S(=O)(=O)c3ccc(OC4CCC4)cc3C(F)(F)F)CN2C(=O)C2(C(F)(F)F)CC2)CC1]

Chiral

In a 10 mL round-bottomed flask, example 7b) (100.0 mg, 185 μmol, Eq: 1.00) was combined with DMA (1.5 mL) to give a light yellow solution. cesium carbonate (72.2 mg, 222 μmol, Eq: 1.20) and cyclobutanol (20.0 mg, 21.7 μl, 277 μmol, Eq: 1.5) were added. The reaction mixture was stirred for 18 h at 25° C. After that, additional cyclobutanol (13.3 mg, 14.5 μl, 185 μmol, Eq: 1.00) was added and the reaction mixture was stirred at 25° C. for 18 h. The crude material was purified by preparative HPLC to yield the title compound as an amorphous colorless solid (31 mg; 28%). m/z=592.3 [M−H]$^−$.

Example 8

(2S,4R)-4-(2-chloro-4-(5-methyl-2H-tetrazol-2-yl)phenylsulfonyl)-N-(1-cyanocyclopropyl)-1-(1-(trifluoromethyl)cyclopropanecarbonyl)pyrrolidine-2-carboxamide

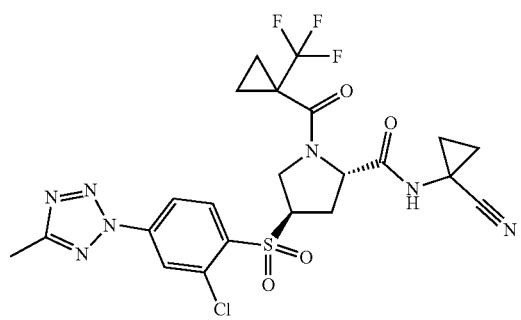

Chiral a) (2S,4R)-4-(2-Chloro-4-fluoro-phenylsulfanyl)-1-(1-trifluoromethyl-cyclopropanecarbonyl)-pyrrolidine-2-carboxylic acid (1-cyano-cyclopropyl)-amide

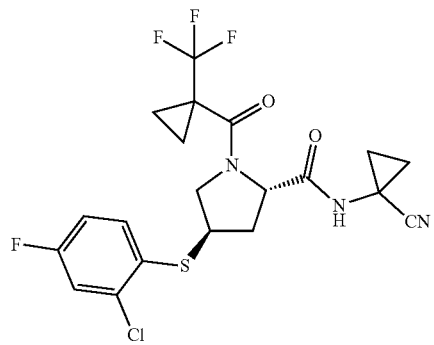 [SMILES: N#CC1(NC(=O)[C@@H]2C[C@@H](Sc3ccc(F)cc3Cl)CN2C(=O)C2(C(F)(F)F)CC2)CC1]

Example 8a) was prepared in analogy to example 7a) starting from example 3d) and 2-chloro-4-fluoro-benzenethiol to yield the title compound as a colorless gum (6.35 g; 96%). m/z=476.1 [M+H]$^+$.

b) (2S,4R)-4-(2-Chloro-4-fluoro-benzenesulfonyl)-1-(1-trifluoromethyl-cyclopropanecarbonyl)-pyrrolidine-2-carboxylic acid (1-cyano-cyclopropyl)-amide

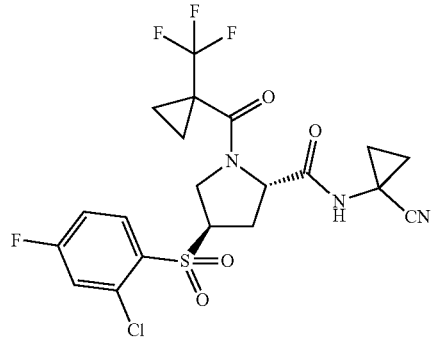 [SMILES: N#CC1(NC(=O)[C@@H]2C[C@@H](S(=O)(=O)c3ccc(F)cc3Cl)CN2C(=O)C2(C(F)(F)F)CC2)CC1]

Example 8b) was prepared in analogy to example 7b) starting from example 8a) to yield the title compound as a white foam (6.55 g; 97%). m/z=508.3 [M+H]$^+$.

c) (2S,4R)-4-(2-chloro-4-(5-methyl-2H-tetrazol-2-yl)phenylsulfonyl)-N-(1-cyanocyclopropyl)-1-(1-(trifluoromethyl)cyclopropanecarbonyl)pyrrolidine-2-carboxamide

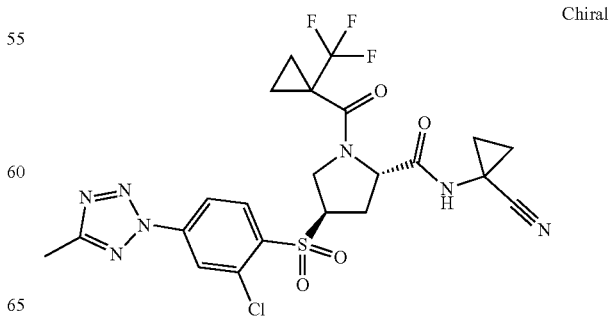

Chiral

In a 10 mL round-bottomed flask, (2S,4R)-4-(2-chloro-4-fluorophenylsulfonyl)-N-(1-cyanocyclopropyl)-1-(1-(trifluoromethyl)cyclopropanecarbonyl)pyrrolidine-2-carboxamide (example 8b)) (400 mg, 788 μmol, Eq: 1.00) was combined with DMA (5 mL) to give a colorless solution. 5-methyl-1H-tetrazole (132 mg, 1.58 mmol, Eq: 2.00) and cesium carbonate (513 mg, 1.58 mmol, Eq: 2.00) were added. The reaction mixture was heated to 80° C. and stirred for 3 h. After that, 5-methyl-1H-tetrazole (13.2 mg, 0.158 mmol, Eq: 0.20) was added and the mixture was stirred at 80° C. for additional 2 h. The reaction mixture was poured into water and extracted with EtOAc (2×). The organic layers were combined, washed with saturated aqueous NaHCO₃ solution (1×), water (3×) and brine (1×). The organic layers were dried over Na₂SO₄ and concentrated in vacuo. The crude material was purified by flash chromatography (silica gel, 20 g, Heptan/AcOEt 2/1, 1/1, 1/2, 1/3) to yield the title compound as a light brown foam (183 mg; 41%). m/z=572.2 [M+H]⁺.

Example 9

(2S,4R)-4-(2-chloro-4-(5-methyl-1H-tetrazol-1-yl)phenylsulfonyl)-N-(1-cyanocyclopropyl)-1-(1-(trifluoromethyl)cyclopropanecarbonyl)pyrrolidine-2-carboxamide

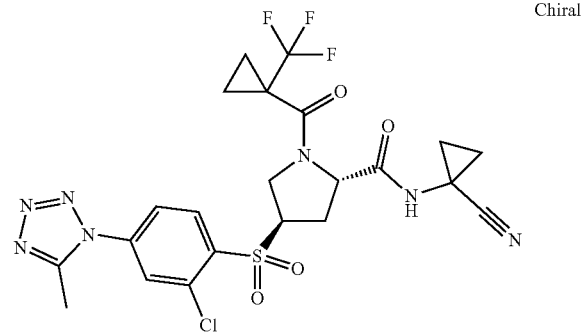 [SMILES: Cc1nnnn1-c1ccc(S(=O)(=O)[C@@H]2C[C@@H](C(=O)NC3(C#N)CC3)N(C(=O)C3(C(F)(F)F)CC3)C2)c(Cl)c1]

Example 9 was obtained as a regioisomer during the synthesis of example 8 as a white foam (198 mg; 44%). m/z=572.2 [M+H]⁺.

Example 10

(2S,4R)-4-(2-chloro-4-(1H-1,2,4-triazol-1-yl)phenylsulfonyl)-N-(1-cyanocyclopropyl)-1-(1-(trifluoromethyl)cyclopropanecarbonyl)pyrrolidine-2-carboxamide

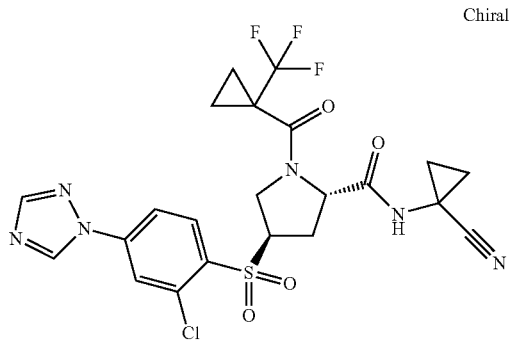 [SMILES: N#CC1(NC(=O)[C@@H]2C[C@@H](S(=O)(=O)c3ccc(-n4cncn4)cc3Cl)CN2C(=O)C2(C(F)(F)F)CC2)CC1]

In a 10 mL round-bottomed flask, (2S,4R)-4-(2-chloro-4-fluorophenylsulfonyl)-N-(1-cyanocyclopropyl)-1-(1-(trifluoromethyl)cyclopropanecarbonyl)pyrrolidine-2-carboxamide (example 8b)) (400 mg, 788 μmol, Eq: 1.00) was combined with DMA (5 mL) to give a colorless solution. 1H-1,2,4-triazole (111 mg, 1.58 mmol, Eq: 2.00) and cesium carbonate (513 mg, 1.58 mmol, Eq: 2.00) were added. The reaction mixture was heated to 80° C. and stirred for 3 h. The reaction mixture was poured into water and extracted with EtOAc (2×). The organic layers were combined, washed with saturated aqueous NaHCO₃ solution (1×), water (3×) and brine (1×). The organic layers were dried over Na₂SO₄ and concentrated in vacuo. The crude material was purified twice by flash chromatography (silica gel, 20 g, DCM/MeOH 98/2, 19/1) and (silica gel, 20 g, Heptan/AcOEt 1/2, 1/3, 1/4) to yield the title compound as a white foam (264 mg; 60%). m/z=557.1 [M+H]⁺.

Example 11

(2S,4R)—N-(1-cyanocyclopropyl)-4-(2,4-di(1H-1,2,4-triazol-1-yl)phenylsulfonyl)-1-(1-(trifluoromethyl)cyclopropanecarbonyl)pyrrolidine-2-carboxamide

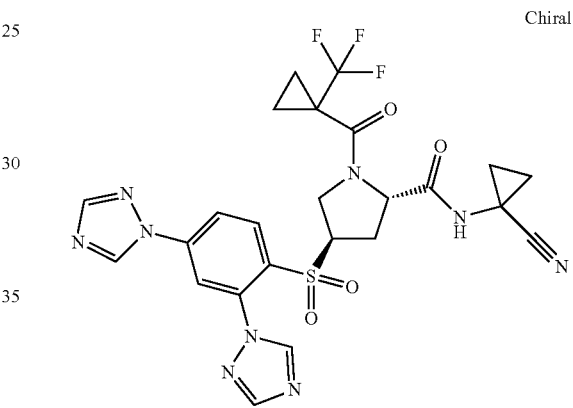

Example 11 was obtained as a byproduct during the synthesis of example 10 as a white solid (34 mg; 7%). m/z=590.1 [M+H]⁺.

Example 12

(2S,4R)-4-(2-chloro-4-(2H-1,2,3-triazol-2-yl)phenylsulfonyl)-N-(1-cyanocyclopropyl)-1-(1-(trifluoromethyl)cyclopropanecarbonyl)pyrrolidine-2-carboxamide

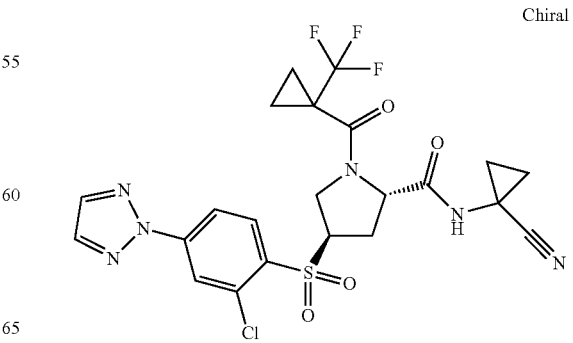

Example 12 was prepared in analogy to example 10 starting from (2S,4R)-4-(2-chloro-4-fluorophenylsulfonyl)-N-(1-cyanocyclopropyl)-1-(1-(trifluoromethyl)cyclopropane-carbonyl)pyrrolidine-2-carboxamide (example 8b)) and 1H-1,2,3-triazole to yield the title compound as a off-white solid (189 mg; 43%). m/z=557.1 [M+H]⁺.

Example 13

(2S,4R)-4-(2-chloro-4-(1H-1,2,3-triazol-1-yl)phenyl-sulfonyl)-N-(1-cyanocyclopropyl)-1-(1-(trifluoromethyl)cyclopropanecarbonyl)pyrrolidine-2-carboxamide

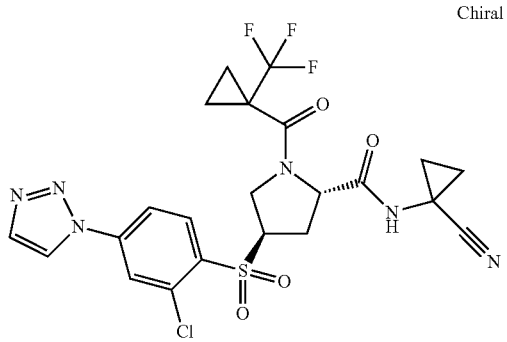 [SMILES: N#CC1(NC(=O)[C@@H]2C[C@@H](S(=O)(=O)c3ccc(-n4ccnn4)cc3Cl)CN2C(=O)C2(C(F)(F)F)CC2)CC1]

Example 13 was obtained as a regioisomer during the synthesis of example 12 as an off-white solid (170 mg; 39%). m/z=557.1 [M+H]⁺.

Example 14

(2S,4R)-4-(2-chloro-4-(3-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide

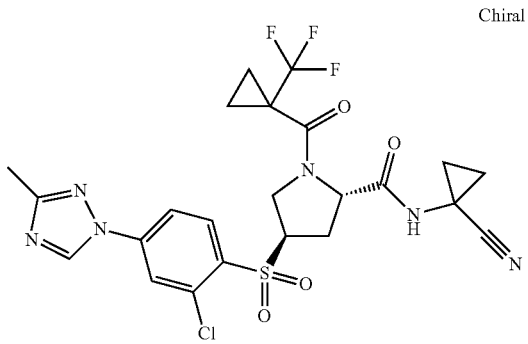 [SMILES: Cc1ncn(-c2ccc(S(=O)(=O)[C@@H]3C[C@@H](C(=O)NC4(C#N)CC4)N(C(=O)C4(C(F)(F)F)CC4)C3)c(Cl)c2)n1]

Example 14 was prepared in analogy to example 10 starting from (2S,4R)-4-(2-chloro-4-fluorophenylsulfonyl)-N-(1-cyanocyclopropyl)-1-(1-(trifluoromethyl)cyclopropane-carbonyl)pyrrolidine-2-carboxamide (example 8b)) and 3-methyl-1H-1,2,4-triazole by stirring the reaction mixture at 22° C. for 16 h to yield the title compound as a white foam (212 mg; 47%). m/z=571.2 [M+H]⁺.

Example 15

(2S,4R)-4-(2-chloro-4-(3,5-dimethyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide

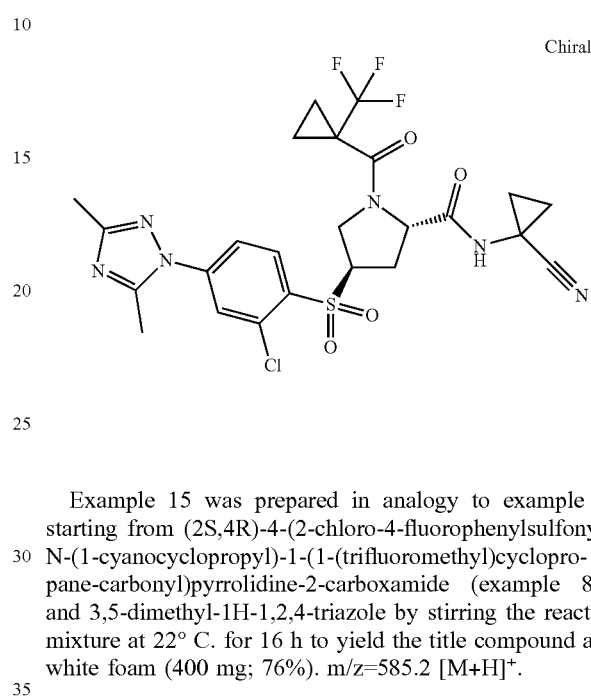

Example 15 was prepared in analogy to example 10 starting from (2S,4R)-4-(2-chloro-4-fluorophenylsulfonyl)-N-(1-cyanocyclopropyl)-1-(1-(trifluoromethyl)cyclopropane-carbonyl)pyrrolidine-2-carboxamide (example 8b)) and 3,5-dimethyl-1H-1,2,4-triazole by stirring the reaction mixture at 22° C. for 16 h to yield the title compound as a white foam (400 mg; 76%). m/z=585.2 [M+H]⁺.

Example 16

(2S,4R)-4-(2-chloro-4-(3-chloro-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide

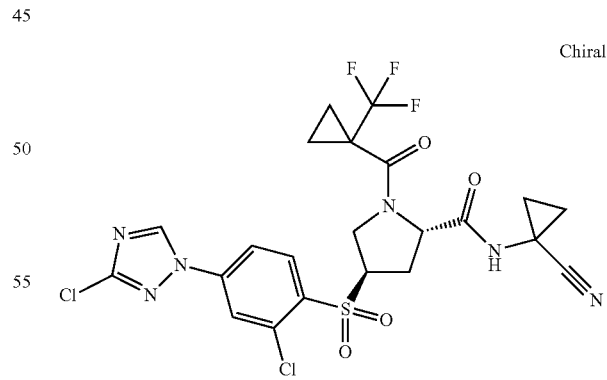

Example 16 was prepared in analogy to example 10 starting from (2S,4R)-4-(2-chloro-4-fluorophenylsulfonyl)-N-(1-cyanocyclopropyl)-1-(1-(trifluoromethyl)cyclopropane-carbonyl)pyrrolidine-2-carboxamide (example 8b)) and 3-chloro-1H-1,2,4-triazole by stirring the reaction mixture at 22° C. for 16 h to yield the title compound as a white foam (432 mg; 81%). m/z=591.2 [M+H]⁺.

Example 17

(2S,4R)-4-(2-chloro-4-(3-(trifluoromethyl)-1H-pyrazol-1-yl)phenylsulfonyl)-N-(1-cyanocyclopropyl)-1-(1-(trifluoromethyl)cyclopropanecarbonyl)pyrrolidine-2-carboxamide

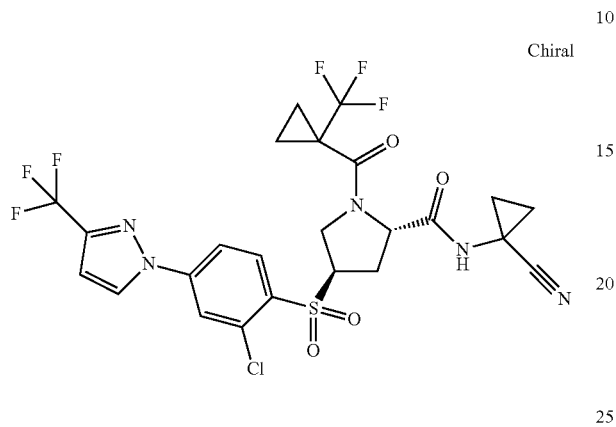

Example 17 was prepared in analogy to example 10 starting from (2S,4R)-4-(2-chloro-4-fluorophenylsulfonyl)-N-(1-cyanocyclopropyl)-1-(1-(trifluoromethyl)cyclopropane-carbonyl)pyrrolidine-2-carboxamide (example 8b)) and 3-(trifluoromethyl)-1H-pyrazole by stirring the reaction mixture at 22° C. for 16 h to yield the title compound as a white foam (419 mg; 76%). m/z=624.1 [M+H]$^+$.

Example 18

(2S,4R)-4-(2-chloro-4-(5-methyl-3-(trifluoromethyl)-1H-pyrazol-1-yl)phenylsulfonyl)-N-(1-cyanocyclopropyl)-1-(1-(trifluoromethyl)cyclopropanecarbonyl)pyrrolidine-2-carboxamide

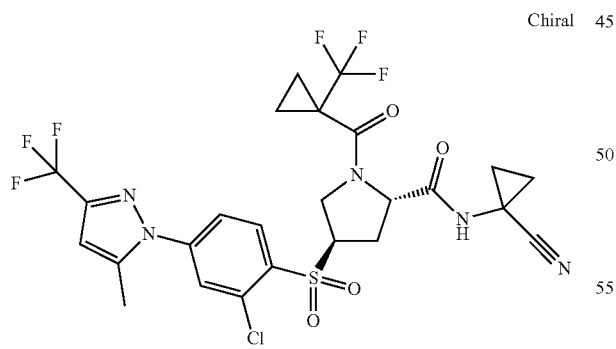

Example 18 was prepared in analogy to example 10 starting from (2S,4R)-4-(2-chloro-4-fluorophenylsulfonyl)-N-(1-cyanocyclopropyl)-1-(1-(trifluoromethyl)cyclopropane-carbonyl)pyrrolidine-2-carboxamide (example 8b)) and 5-methyl-3-(trifluoromethyl)-1H-pyrazole by stirring the reaction mixture at 22° C. for 16 h to yield the title compound as a white foam (411 mg; 73%). m/z=638.1 [M+H]$^+$.

Example 19

(2S,4R)—N-(1-cyanocyclopropyl)-4-(2-methyl-4-(3-(trifluoromethyl)-1H-pyrazol-1-yl)phenylsulfonyl)-1-(1-(trifluoromethyl)cyclopropanecarbonyl)pyrrolidine-2-carboxamide

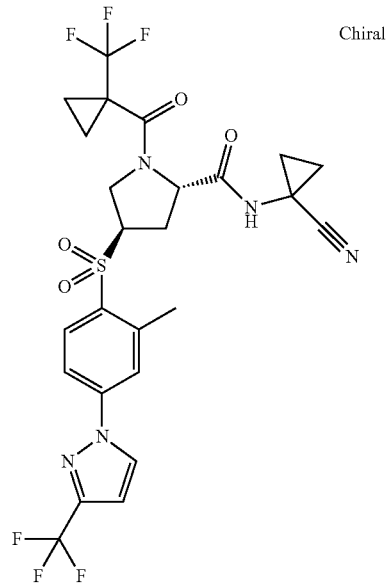 [SMILES: Cc1cc(-n2ccc(C(F)(F)F)n2)ccc1S(=O)(=O)[C@@H]1C[C@@H](C(=O)NC2(C#N)CC2)N(C(=O)C2(C(F)(F)F)CC2)C1]

a) (2S,4R)—N-(1-cyanocyclopropyl)-4-(4-fluoro-2-methylphenylthio)-1-(1-(trifluoromethyl)cyclopropanecarbonyl)pyrrolidine-2-carboxamide

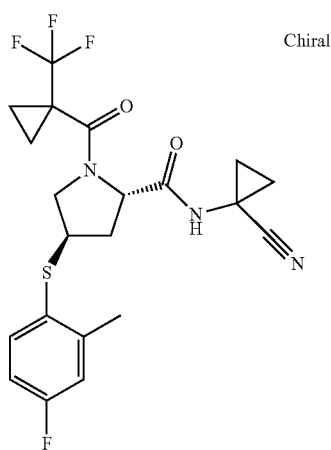 [SMILES: Cc1cc(F)ccc1S[C@@H]1C[C@@H](C(=O)NC2(C#N)CC2)N(C(=O)C2(C(F)(F)F)CC2)C1]

The title compound was prepared in analogy to example 3, step e), using 4-fluoro-2-methylbenzenethiol, and obtained as a light brown gum (3.47 g, 97%). m/z=456.4 [M+H]$^+$.

b) (2S,4R)—N-(1-cyanocyclopropyl)-4-(4-fluoro-2-methylphenylsulfonyl)-1-(1-(trifluoromethyl)cyclopropanecarbonyl)pyrrolidine-2-carboxamide

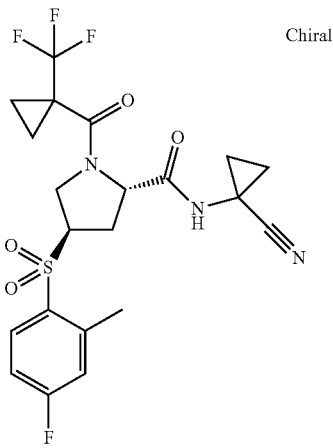 [SMILES: Cc1cc(F)ccc1S(=O)(=O)[C@@H]1C[C@@H](C(=O)NC2(C#N)CC2)N(C(=O)C2(C(F)(F)F)CC2)C1]

The title compound was prepared in analogy to example 3, step f) from (2S,4R)—N-(1-cyanocyclopropyl)-4-(4-fluoro-2-methylphenylthio)-1-(1-(trifluoromethyl)cyclopropanecarbonyl)pyrrolidine-2-carboxamide (example 19a) and obtained as a white foam (2.84 g, 76%). m/z=487.1202 [M+].

c) (2S,4R)—N-(1-cyanocyclopropyl)-4-(2-methyl-4-(3-(trifluoromethyl)-1H-pyrazol-1-yl)phenylsulfonyl)-1-(1-(trifluoromethyl)cyclopropanecarbonyl)pyrrolidine-2-carboxamide

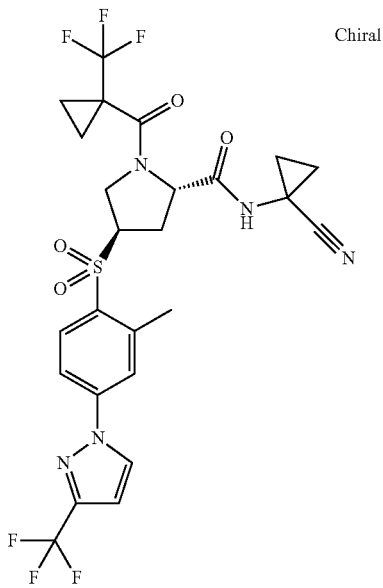 [SMILES: Cc1cc(-n2ccc(C(F)(F)F)n2)ccc1S(=O)(=O)[C@@H]1C[C@@H](C(=O)NC2(C#N)CC2)N(C(=O)C2(C(F)(F)F)CC2)C1]

(2S,4R)—N-(1-Cyanocyclopropyl)-4-(4-fluoro-2-methylphenyl sulfonyl)-1-(1-(trifluoromethyl)cyclopropanecarbonyl)pyrrolidine-2-carboxamide (example 19b, 70 mg, 144 µmol), 3-(trifluoromethyl)-1H-pyrazole (39.1 mg, 287 µmol) and cesium carbonate (93.6 mg, 287 µmol) were combined with N,N-dimethylacetamide (1.00 mL) in a sealed tube to give a white suspension. The reaction was stirred over the weekend at ambient temperature. After filtration, the title compound was isolated from the reaction mixture by preparative HPLC (zorbax C18 21.2×50 mm; flow: 20 mL/min; gradient: acetonitrile/water (+0.1% formic acid)=(95%-5% to 5%-95%) in 7.5 min; collected by 254 nm detector; 28.8 mg, 33.2%). m/z=604.14 [M+H+].

Example 20

(2S,4R)—N-(1-cyanocyclopropyl)-4-(2'-(trifluoromethoxy)biphenyl-4-ylsulfonyl)-1-(1-(trifluoromethyl)cyclopropanecarbonyl)pyrrolidine-2-carboxamide

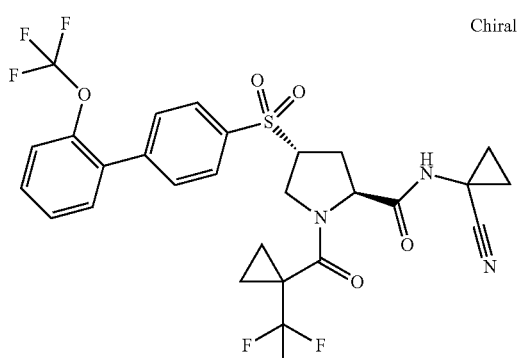

a) (2S,4R)-4-(4-bromophenylthio)-N-(1-cyanocyclopropyl)-1-(1-(trifluoromethyl)cyclopropanecarbonyl)pyrrolidine-2-carboxamide

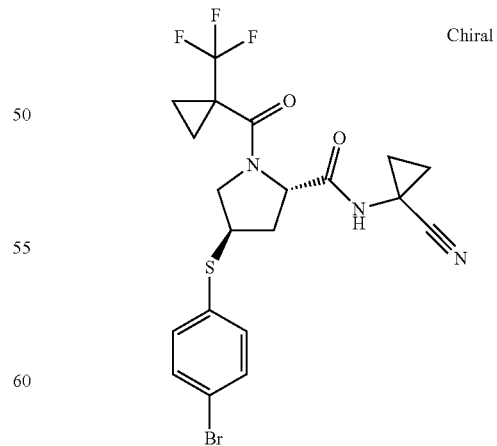

The title compound was prepared in analogy to example 3, step e), using 4-bromobenzenethiol, and obtained as a colorless foam (952 mg, 95%). m/z=502.1/504.0 [M+H]+.

b) (2S,4R)-4-(4-bromophenylsulfonyl)-N-(1-cyanocyclopropyl)-1-(1-(trifluoromethyl)cyclopropanecarbonyl)pyrrolidine-2-carboxamide

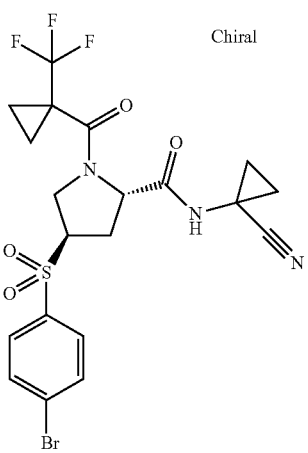 [SMILES: N#CC1(NC(=O)[C@@H]2C[C@@H](S(=O)(=O)c3ccc(Br)cc3)CN2C(=O)C2(C(F)(F)F)CC2)CC1]

The title compound was prepared in analogy to example 3, step f) from (2S,4R)-4-(4-bromophenylthio)-N-(1-cyanocyclopropyl)-1-(1-(trifluoromethyl)cyclopropanecarbonyl)pyrrolidine-2-carboxamide (example 20a) and obtained as a white powder (918 mg, 91%). m/z=532.0/534.0 [M–H]⁻.

c) (2S,4R)—N-(1-cyanocyclopropyl)-4-(2'-(trifluoromethoxy)biphenyl-4-ylsulfonyl)-1-(1-(trifluoromethyl)cyclopropanecarbonyl)pyrrolidine-2-carboxamide

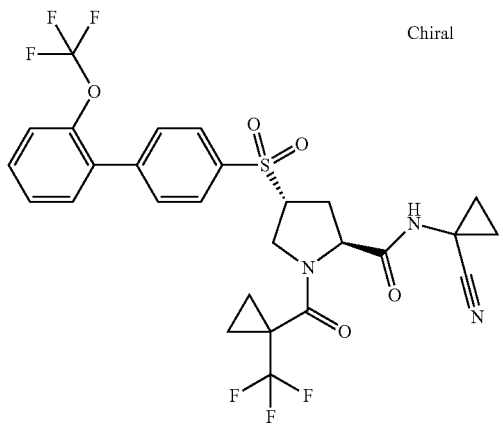 [SMILES: N#CC1(NC(=O)[C@@H]2C[C@@H](S(=O)(=O)c3ccc(-c4ccccc4OC(F)(F)F)cc3)CN2C(=O)C2(C(F)(F)F)CC2)CC1]

To a solution of (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b, 321 mg, 0.6 mmol) and 2-(trifluoromethoxy)phenylboronic acid (185 mg, 900 µmol) in dioxan (6 mL) and sodium carbonate 2M in water (1.5 mL, 3.00 mmol) was added under stirring and under an atmosphere of nitrogen 1,1'-bis)diphenylphosphino)-ferrocene-palladium(II)dichloride dichloromethane complex (24.5 mg, 30.0 µmol). The reaction was heated to 85° C. over night. After cooling water was added and the reaction was extracted twice with ethyl acetate. The combined organic layers were washed with saturated aqueous sodium chloride solution, dried over sodium sulfate, filtered and the solvent was removed under reduced pressure. The residue was purified by column chromatography on silica gel using heptane:ethyl acetate (9:1 to 1:4) as the eluent. The crude product was stirred with heptane/diethyl ether, filtered and dried to yield the title compound as a white powder (272.4 mg, 74%). m/z=614.1 [M–H]⁻.

Example 21

(2S,4R)-4-(2-chloro-4-cyclobutoxyphenylsulfonyl)-N-(1-cyanocyclopropyl)-1-(1-(trifluoromethyl)cyclopropanecarbonyl)pyrrolidine-2-carboxamide

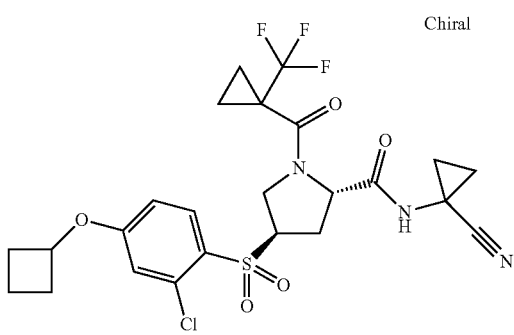 [SMILES: N#CC1(NC(=O)[C@@H]2C[C@@H](S(=O)(=O)c3ccc(OC4CCC4)cc3Cl)CN2C(=O)C2(C(F)(F)F)CC2)CC1]

Example 21 was prepared in analogy to example 10 starting from (2S,4R)-4-(2-chloro-4-fluorophenylsulfonyl)-N-(1-cyanocyclopropyl)-1-(1-(trifluoromethyl)cyclopropane-carbonyl)pyrrolidine-2-carboxamide (example 8b)) and cyclobutanol by stirring the reaction mixture at 22° C. for 16 h to yield the title compound as a white foam (166 mg; 60%). m/z=560.2 [M+H]⁺.

Example 22

(2S,4R)—N-(1-cyanocyclopropyl)-4-(3-methyl-2'-(trifluoromethoxy)biphenyl-4-ylsulfonyl)-1-(1-(trifluoromethyl)cyclopropanecarbonyl)pyrrolidine-2-carboxamide

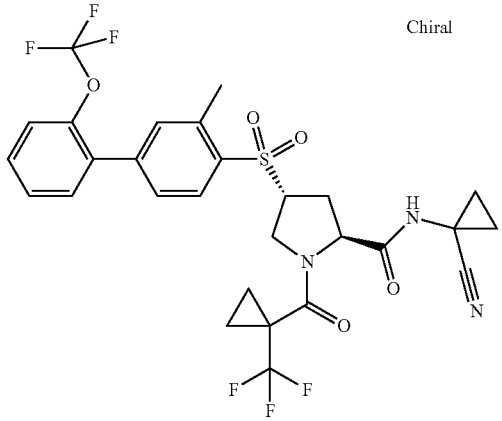 [SMILES: Cc1cc(-c2ccccc2OC(F)(F)F)ccc1S(=O)(=O)[C@@H]1C[C@@H](C(=O)NC2(C#N)CC2)N(C(=O)C2(C(F)(F)F)CC2)C1]

a) (2S,4R)-4-(4-bromo-2-methylphenylthio)-N-(1-cyanocyclopropyl)-1-(1-(trifluoromethyl)cyclopropanecarbonyl)pyrrolidine-2-carboxamide

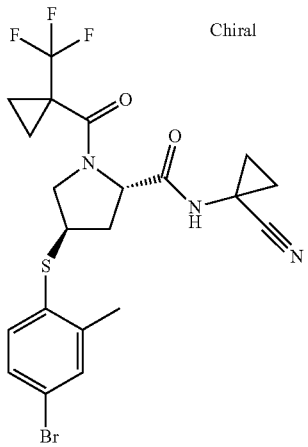 [SMILES: Cc1cc(Br)ccc1S[C@@H]1C[C@@H](C(=O)NC2(C#N)CC2)N(C(=O)C2(C(F)(F)F)CC2)C1]

The title compound was prepared in analogy to example 3, step e), using 4-bromobenzenethiol, and obtained as a colorless oil (1087 mg, 89%). m/z=516.1/518.3 [M+H]$^+$.

b) (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide

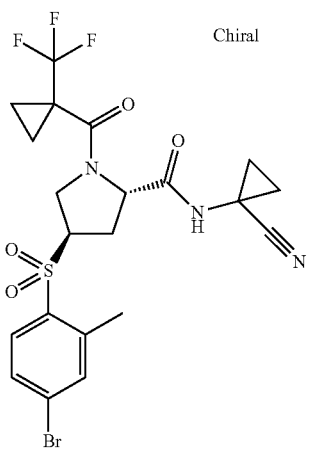 [SMILES: Cc1cc(Br)ccc1S(=O)(=O)[C@@H]1C[C@@H](C(=O)NC2(C#N)CC2)N(C(=O)C2(C(F)(F)F)CC2)C1]

The title compound was prepared in analogy to example 3, step f) from (2S,4R)-4-(4-bromo-2-methylphenylthio)-N-(1-cyanocyclopropyl)-1-(1-(trifluoromethyl)cyclopropanecarbonyl)pyrrolidine-2-carboxamide (example 22a) and 2-(trifluoromethoxy)phenylboronic acid and obtained as a colorless waxy solid (1.05 g, 93%). m/z=550.2/548.2 [M+H]$^+$.

c) (2S,4R)—N-(1-cyanocyclopropyl)-4-(3-methyl-2'-(trifluoromethoxy)biphenyl-4-ylsulfonyl)-1-(1-(trifluoromethyl)cyclopropanecarbonyl)pyrrolidine-2-carboxamide

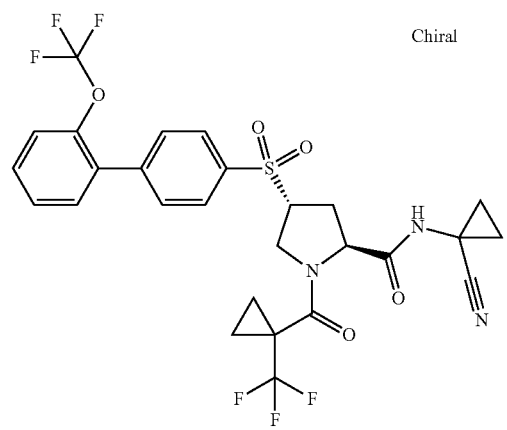 [SMILES: N#CC1(NC(=O)[C@@H]2C[C@@H](S(=O)(=O)c3ccc(-c4ccccc4OC(F)(F)F)cc3)CN2C(=O)C2(C(F)(F)F)CC2)CC1]

The title compound was prepared in analogy to example 20, step c) from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22a) and obtained as a off-white foam (179 mg, 57%). m/z=630.3 [M+H]$^+$.

Example 23

(2S,4R)-4-[4-(5-Methyl-3-trifluoromethyl-pyrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

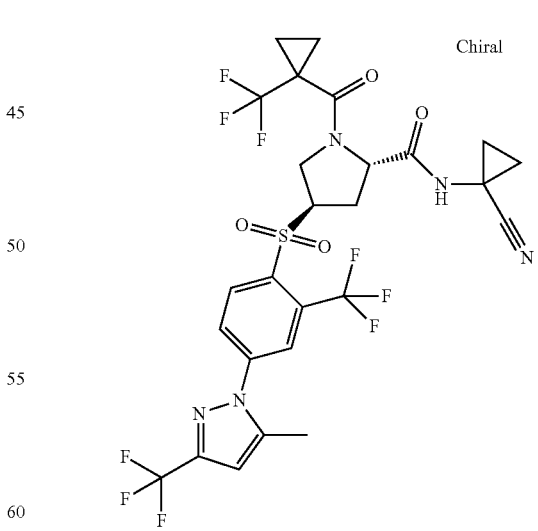

Example 23 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 5-methyl-3-(trifluoromethyl)-1H-pyrazole by stirring the reaction mixture at 22° C. for 72 h to yield the title compound as a colorless foam (104 mg; 84%). m/z=672.1325 [M+H]⁺.

Example 24

(2S,4R)-4-[4-(3-Methyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

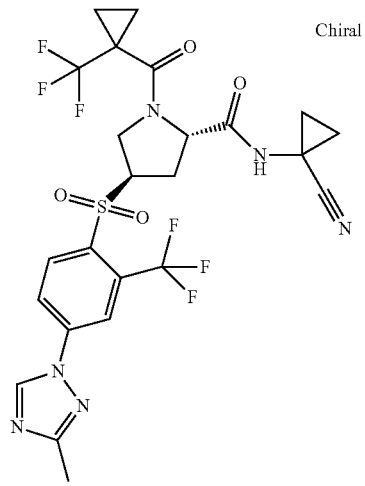 [SMILES: Cc1ncn(-c2ccc(S(=O)(=O)[C@@H]3C[C@@H](C(=O)NC4(C#N)CC4)N(C(=O)C4(C(F)(F)F)CC4)C3)c(C(F)(F)F)c2)n1]

Example 24 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 3-methyl-1H-1,2,4-triazole by stirring the reaction mixture at 22° C. for 72 h to yield the title compound as a colorless amorphous solid (26 mg; 23%). m/z=605.1390 [M+H]⁺.

Example 25

(2S,4R)-4-[4-(3-Methyl-[1,2,4]triazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

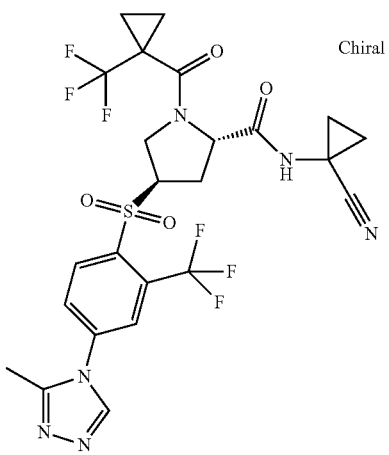 [SMILES: Cc1nncn1-c1ccc(S(=O)(=O)[C@@H]2C[C@@H](C(=O)NC3(C#N)CC3)N(C(=O)C3(C(F)(F)F)CC3)C2)c(C(F)(F)F)c1]

Example 25 was obtained as a regioisomer during the synthesis of example 24 to yield the title compound as a colorless amorphous solid (1.5 mg; 1.3%). m/z=605.1398 [M+H]⁺.

Example 26

(2S,4R)-4-(4-(1H-1,2,4-triazol-1-yl)-2-(trifluoromethyl)phenylsulfonyl)-N-(1-cyanocyclopropyl)-1-(1-(trifluoromethyl)cyclopropanecarbonyl)pyrrolidine-2-carboxamide

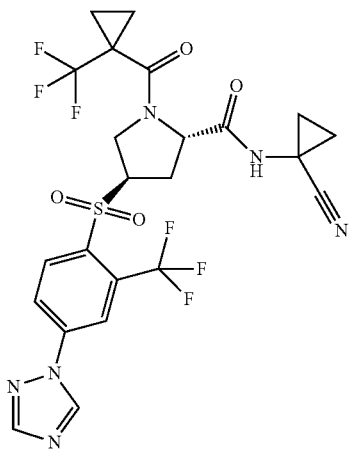 [SMILES: N#CC1(NC(=O)[C@@H]2C[C@@H](S(=O)(=O)c3ccc(-n4cncn4)cc3C(F)(F)F)CN2C(=O)C2(C(F)(F)F)CC2)CC1]

Example 26 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 1H-1,2,4-triazole by stirring the reaction mixture at 22° C. for 4 h to yield the title compound as a colorless amorphous solid (68 mg; 31%). m/z=589.1110 [M+H]⁻.

Example 27

(2S,4R)-4-[4-(3,5-Dimethyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

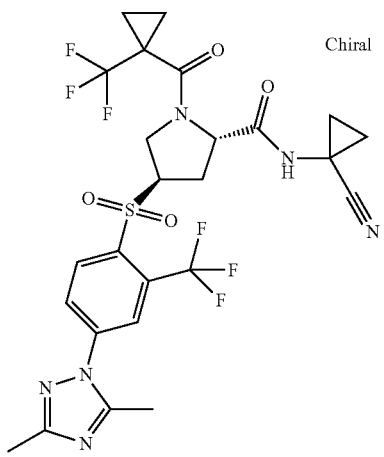 [SMILES: Cc1nc(C)n(-c2ccc(S(=O)(=O)[C@@H]3C[C@@H](C(=O)NC4(C#N)CC4)N(C(=O)C4(C(F)(F)F)CC4)C3)c(C(F)(F)F)c2)n1]

Example 27 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 3,5-dimethyl-1H-1,2,4-triazole by stirring the reaction mixture at 22° C. for 4 h to yield the title compound as a colorless foam (122 mg; 53%). m/z=619.1553 [M+H]$^+$.

Example 28

(2S,4R)—N-(1-cyanocyclopropyl)-4-(4-(1-methyl-3-(trifluoromethyl)-1H-pyrazol-5-yl)phenylsulfonyl)-1-(1-(trifluoromethyl)cyclopropanecarbonyl)pyrrolidine-2-carboxamide

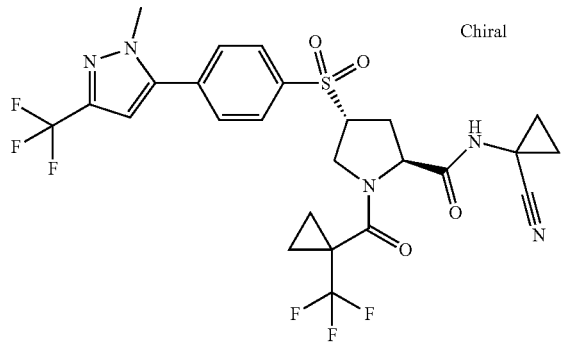 [SMILES: Cn1nc(C(F)(F)F)cc1-c1ccc(S(=O)(=O)[C@@H]2C[C@@H](C(=O)NC3(C#N)CC3)N(C(=O)C3(C(F)(F)F)CC3)C2)cc1]

The title compound was prepared in analogy to example 20, step c) from (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b) and 1-methyl-5-(4,4,5,5-tetramethyl-1,3,2-dioxaborolan-2-yl)-3-(trifluoromethyl)-1H-pyrazole and obtained as a white solid (31 mg, 8%) after purification on preparative HPLC. m/z=602.2 [M−H]$^-$.

Example 29

(2S,4R)—N-(1-cyanocyclopropyl)-4-(2'-formyl-3-methylbiphenyl-4-ylsulfonyl)-1-(1-(trifluoromethyl)cyclopropanecarbonyl)pyrrolidine-2-carboxamide

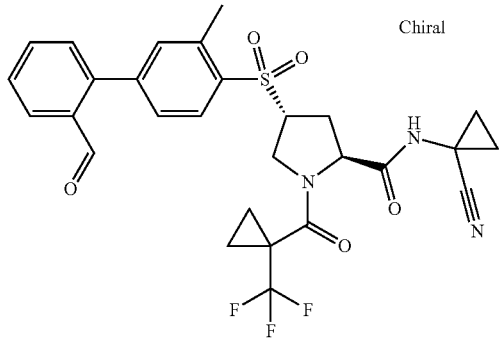 [SMILES: Cc1cc(-c2ccccc2C=O)ccc1S(=O)(=O)[C@@H]1C[C@@H](C(=O)NC2(C#N)CC2)N(C(=O)C2(C(F)(F)F)CC2)C1]

The title compound was prepared in analogy to example 20, step c) from (2S,4R)-4-(4-bromo-2-methylphenylsulfonyl)-N-(1-cyanocyclopropyl)-1-(1-(trifluoromethyl)cyclo- propanecarbonyl)pyrrolidine-2-carboxamide (example 22b) and 2-formylphenylboronic acid and obtained as a white solid (146 mg, 51%). m/z=574.2 [M+H]$^+$.

Example 30

(2S,4R)-4-[4-(3-Chloro-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

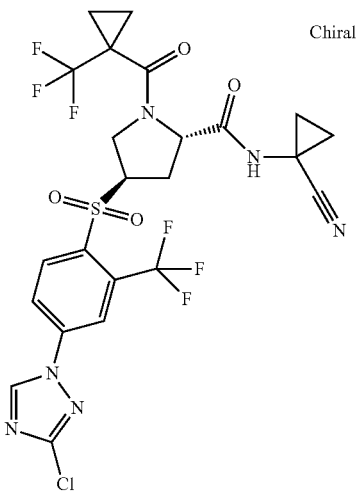 [SMILES: N#CC1(NC(=O)[C@@H]2C[C@@H](S(=O)(=O)c3ccc(-n4cnc(Cl)n4)cc3C(F)(F)F)CN2C(=O)C2(C(F)(F)F)CC2)CC1]

Example 30 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 3-chloro-1H-1,2,4-triazole by stirring the reaction mixture at 22° C. for 4 h to yield the title compound as a colorless foam (135 mg; 59%). m/z=623.0708 [M+H]$^+$.

Example 31

(2S,4R)—N-(1-cyanocyclopropyl)-4-(4-(5-methyl-1H-1,2,4-triazol-1-yl)-2-(trifluoromethyl)phenylsulfonyl)-1-(1-(trifluoromethyl)cyclopropanecarbonyl)pyrrolidine-2-carboxamide

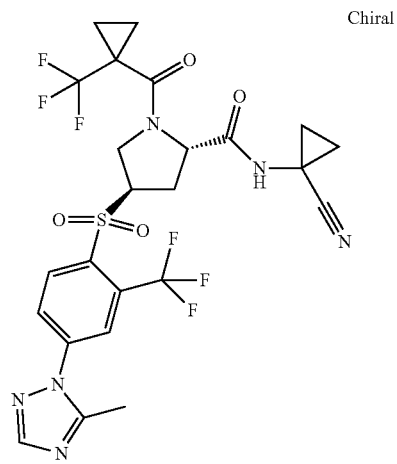 [SMILES: Cc1ncnn1-c1ccc(S(=O)(=O)[C@@H]2C[C@@H](C(=O)NC3(C#N)CC3)N(C(=O)C3(C(F)(F)F)CC3)C2)c(C(F)(F)F)c1]

Example 31 was obtained as a regioisomer during the synthesis of example 24 to yield the title compound as a colorless amorphous solid (26 mg; 23%). m/z=605.1397 [M+H]⁺.

Example 32

(2S,4R)—N-(1-cyanocyclopropyl)-4-(2-methyl-4-(1-methyl-3-(trifluoromethyl)-1H-pyrazol-5-yl)phenylsulfonyl)-1-(1-(trifluoromethyl)cyclopropanecarbonyl) pyrrolidine-2-carboxamide

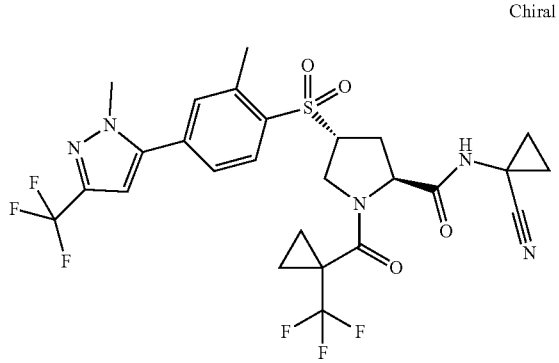 [SMILES: Cc1cc(-c2cc(C(F)(F)F)nn2C)ccc1S(=O)(=O)[C@@H]1C[C@@H](C(=O)NC2(C#N)CC2)N(C(=O)C2(C(F)(F)F)CC2)C1]

The title compound was prepared in analogy to example 20, step c) from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 1-methyl-5-(4,4,5,5-tetramethyl-1,3,2-dioxaborolan-2-yl)-3-(trifluoromethyl)-1H-pyrazole and obtained as a off-white solid (16 mg, 5%) after purification on preparative HPLC. m/z=618.3 [M+H]⁺.

Example 33

(2S,4R)—N-(1-cyanocyclopropyl)-4-(4-(3,5-dimethyl-1H-1,2,4-triazol-1-yl)phenylsulfonyl)-1-(1-(trifluoromethyl)cyclopropanecarbonyl)pyrrolidine-2-carboxamide

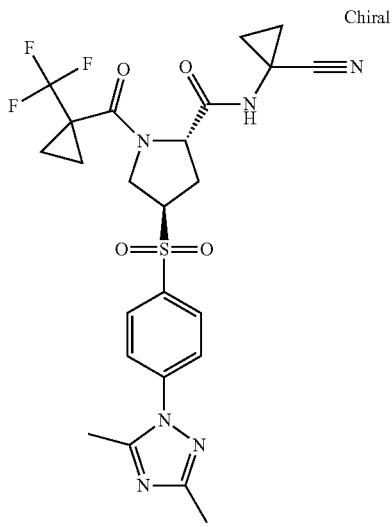 [SMILES: Cc1nc(C)n(-c2ccc(S(=O)(=O)[C@@H]3C[C@@H](C(=O)NC4(C#N)CC4)N(C(=O)C4(C(F)(F)F)CC4)C3)cc2)n1]

a) (2S,4R)—N-(1-cyanocyclopropyl)-4-(4-fluorophenylthio)-1-(1-(trifluoromethyl)cyclopropanecarbonyl)pyrrolidine-2-carboxamide

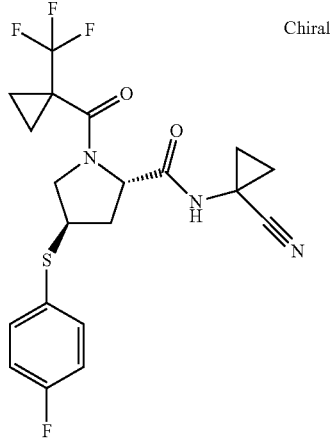 [SMILES: N#CC1(NC(=O)[C@@H]2C[C@@H](Sc3ccc(F)cc3)CN2C(=O)C2(C(F)(F)F)CC2)CC1]

The title compound was prepared in analogy to example 3, step e), using 4-fluorobenzenethiol, and obtained as a off-white foam (2.72 g, 72%). m/z=442.2 [M+H⁺].

b) (2S,4R)—N-(1-cyanocyclopropyl)-4-(4-fluorophenylsulfonyl)-1-(1-(trifluoromethyl)cyclopropanecarbonyl)pyrrolidine-2-carboxamide

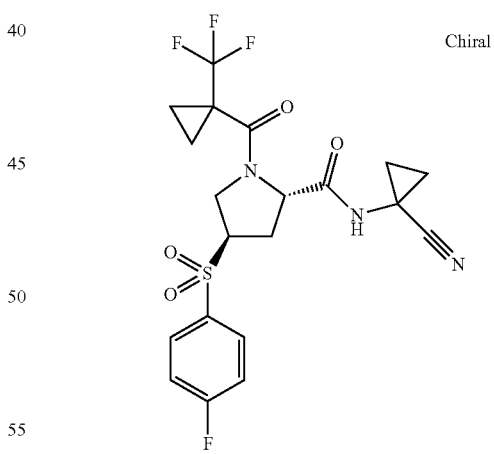

The title compound was prepared in analogy to example 3, step f) from (2S,4R)—N-(1-cyanocyclopropyl)-4-(4-fluorophenylthio)-1-(1-(trifluoromethyl)cyclopropanecarbonyl) pyrrolidine-2-carboxamide (example 33a) and obtained as a white foam (840 mg, 29%). m/z=474.11 [M+H⁺].

c) (2S,4R)—N-(1-cyanocyclopropyl)-4-(4-(3,5-dimethyl-1H-1,2,4-triazol-1-yl)phenylsulfonyl)-1-(1-(trifluoromethyl)cyclopropanecarbonyl)pyrrolidine-2-carboxamide

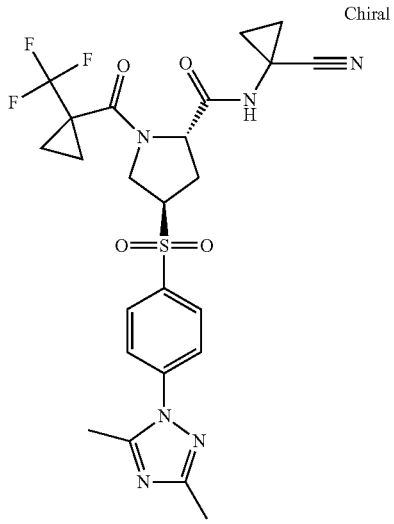 [SMILES: Cc1nc(C)n(-c2ccc(S(=O)(=O)[C@@H]3C[C@@H](C(=O)NC4(C#N)CC4)N(C(=O)C4(C(F)(F)F)CC4)C3)cc2)n1]

Under an atmosphere of argon, (2S,4R)—N-(1-cyanocyclopropyl)-4-(4-fluorophenylsulfonyl)-1-(1-(trifluoromethyl)cyclopropanecarbonyl)pyrrolidine-2-carboxamide (example 33, step b, 0.1 g, 211 µmol) was combined with N,N-dimethylacetamide (2.00 mL) to give a colorless suspension. 3,5-Dimethyl-1H-1,2,4-triazole (41.0 mg, 422 µmol) and cesium carbonate (138 mg, 422 µmol) were added. The reaction mixture was stirred over the weekend at ambient temperature. The crude material was purified by preparative HPLC (Zorbax Eclipse XDB-C18; 21.2×50 mm; flow: 25 mL/min; gradient: acetonitrile/water (+0.1% formic acid)=(95%-5% to 5%-95%) in 6 min; collected by 254 nm detector) to yield the title compound as a colorless viscous oil (13.2 mg, 11.4%). m/z=551.17 [M+H$^+$].

Example 34

(2S,4R)-4-(4-(1H-1,2,3-triazol-1-yl)phenylsulfonyl)-N-(1-cyanocyclopropyl)-1-(1-(trifluoromethyl)cyclopropanecarbonyl)pyrrolidine-2-carboxamide

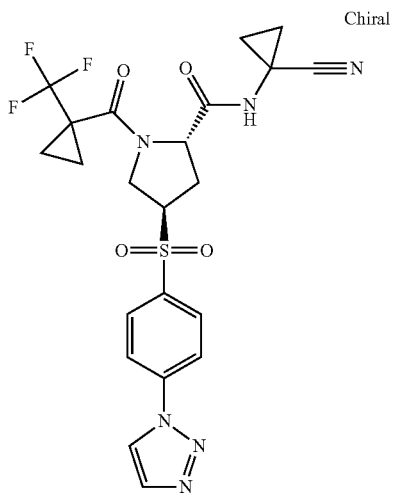 [SMILES: N#CC1(NC(=O)[C@@H]2C[C@@H](S(=O)(=O)c3ccc(-n4ccnn4)cc3)CN2C(=O)C2(C(F)(F)F)CC2)CC1]

The title compound was prepared in analogy to example 33, using 1H-1,2,3-triazole in step c), and was obtained as a colorless viscous oil (2.5 mg, 2.83%). m/z=523.13 [M+H$^+$]).

Example 35

(2S,4R)—N-(1-cyanocyclopropyl)-4-(4-(3-(trifluoromethyl)-1H-pyrazol-1-yl)phenylsulfonyl)-1-(1-(trifluoromethyl)cyclopropanecarbonyl)pyrrolidine-2-carboxamide

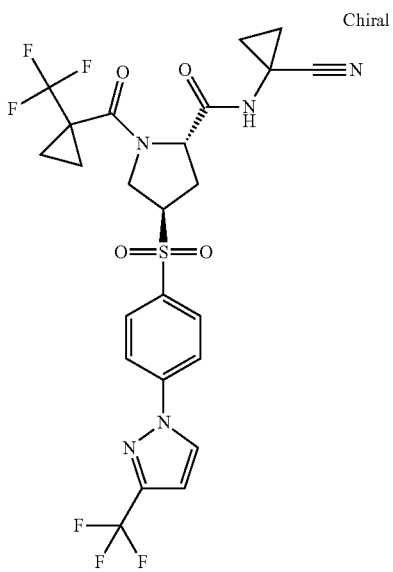 [SMILES: N#CC1(NC(=O)[C@@H]2C[C@@H](S(=O)(=O)c3ccc(-n4ccc(C(F)(F)F)n4)cc3)CN2C(=O)C2(C(F)(F)F)CC2)CC1]

The title compound was prepared in analogy to example 33, using 3-(trifluoromethyl)-1H-pyrazole in step c), and was obtained as a white solid (38.2 mg, 38.3%). m/z=590.13 [M+H$^+$].

Example 36

(2S,4R)—N-(1-cyanocyclopropyl)-4-(4-(5-methyl-3-(trifluoromethyl)-1H-pyrazol-1-yl)phenylsulfonyl)-1-(1-(trifluoromethyl)cyclopropanecarbonyl)pyrrolidine-2-carboxamide

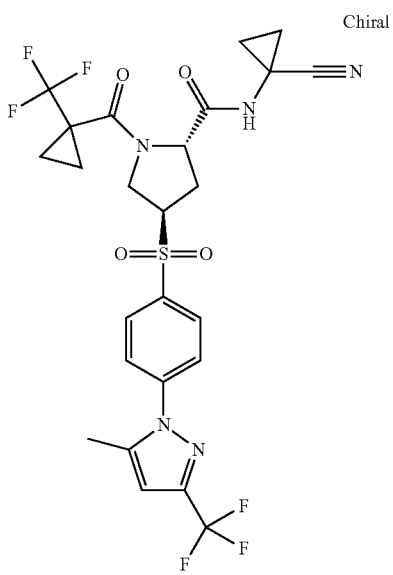 [SMILES: Cc1cc(C(F)(F)F)nn1-c1ccc(S(=O)(=O)[C@@H]2C[C@@H](C(=O)NC3(C#N)CC3)N(C(=O)C3(C(F)(F)F)CC3)C2)cc1]

The title compound was prepared in analogy to example 33, using 5-methyl-3-(trifluoromethyl)-1H-pyrazole in step c), and was obtained as a white solid (22.1 mg, 21.7%). m/z=604.14 [M+H⁺]).

Example 37

(2S,4R)—N-(1-cyanocyclopropyl)-4-(2'-formylbiphenyl-4-ylsulfonyl)-1-(1-(trifluoromethyl)cyclopropanecarbonyl)pyrrolidine-2-carboxamide

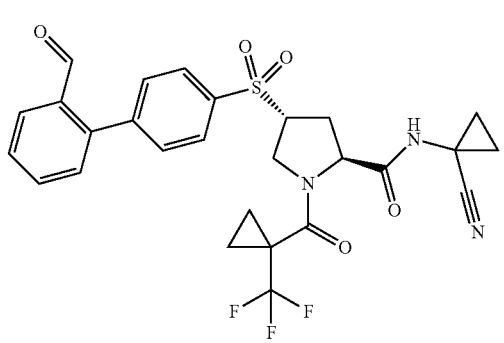

The title compound was prepared in analogy to example 20, step c) from (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b) and 2-formylphenylboronic acid and obtained as a white powder (57.6 mg, 52%). m/z=558.2 [M–H]⁻.

Example 38

(2S,4R)—N-(1-cyanocyclopropyl)-4-(2'-ethoxybiphenyl-4-ylsulfonyl)-1-(1-(trifluoromethyl)cyclopropanecarbonyl)pyrrolidine-2-carboxamide

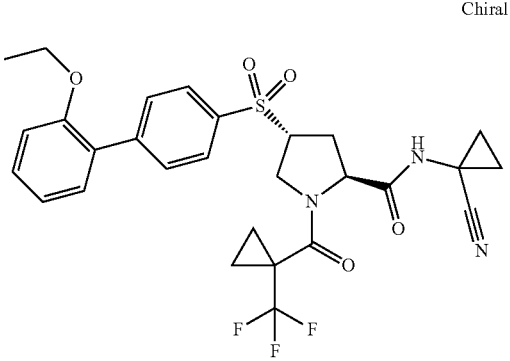 [SMILES: CCOc1ccccc1-c1ccc(S(=O)(=O)[C@@H]2C[C@@H](C(=O)NC3(C#N)CC3)N(C(=O)C3(C(F)(F)F)CC3)C2)cc1]

The title compound was prepared in analogy to example 20, step c) from (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b) and 2-ethoxyphenylboronic acid and obtained as a pink powder (86.1 mg, 75%). m/z=574.2 [M–H]⁻.

Example 39

(2S,4R)-4-(4-(2-aminopyrimidin-5-yl)phenylsulfonyl)-N-(1-cyanocyclopropyl)-1-(1-(trifluoromethyl)cyclopropanecarbonyl)pyrrolidine-2-carboxamide

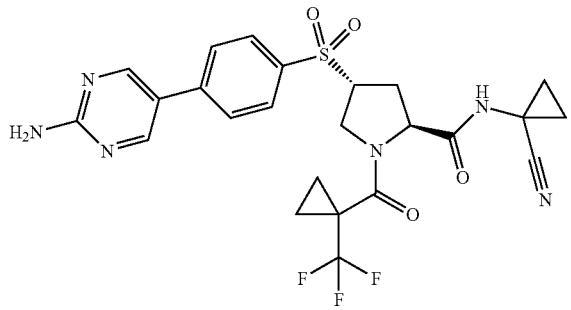

The title compound was prepared in analogy to example 20, step c) from (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b) and 2-aminopyrimidin-5-ylboronic acid and obtained as a white powder (72 mg, 66%). m/z=547.2 [M–H]⁻.

Example 40

(2S,4R)—N-(1-cyanocyclopropyl)-4-(2'-ethoxy-3-methylbiphenyl-4-ylsulfonyl)-1-(1-(trifluoromethyl)cyclopropanecarbonyl)pyrrolidine-2-carboxamide

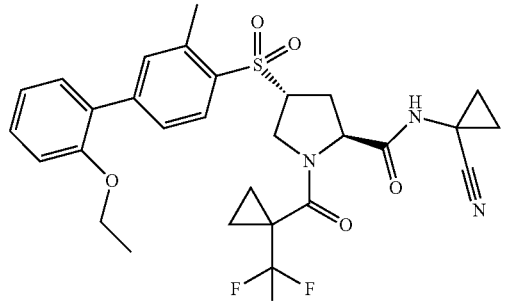

The title compound was prepared in analogy to example 20, step c) from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 2-ethoxyphenylboronic acid and obtained as a off-white solid (255 mg, 87%). m/z=590.4 [M+H]⁺.

Example 41

(2S,4R)-4-(2'-cyano-3-methylbiphenyl-4-ylsulfonyl)-N-(1-cyanocyclopropyl)-1-(1-(trifluoromethyl)cyclopropanecarbonyl)pyrrolidine-2-carboxamide

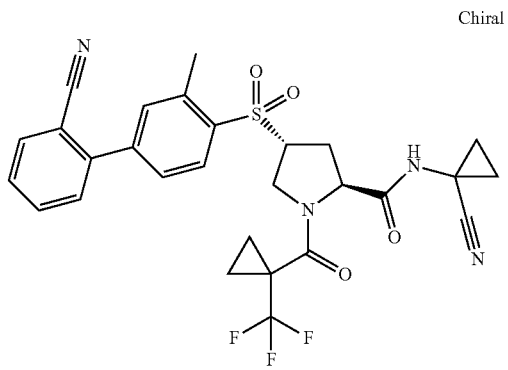 [SMILES: Cc1cc(-c2ccccc2C#N)ccc1S(=O)(=O)[C@@H]1C[C@@H](C(=O)NC2(C#N)CC2)N(C(=O)C2(C(F)(F)F)CC2)C1]

The title compound was prepared in analogy to example 20, step c) from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 2-(4,4,5,5-tetramethyl-1,3,2-dioxaborolan-2-yl)benzonitrile and obtained as a off-white solid (43.2 mg, 12%) after purification on preparative HPLC. m/z=571.2 [M+H]+.

Example 42

(2S,4R)—N-(1-cyanocyclopropyl)-4-(2'-ethoxy-4',5'-difluoro-3-methylbiphenyl-4-ylsulfonyl)-1-(1-(trifluoromethyl)cyclopropanecarbonyl)pyrrolidine-2-carboxamide

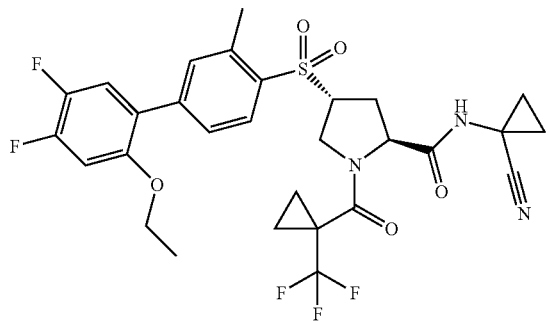

The title compound was prepared in analogy to example 20, step c) from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 2-ethoxy-4,5-difluorophenylboronic acid and obtained as a off-white solid (235.5 mg, 75%) after purification on preparative HPLC. m/z=626.3 [M+H]+.

Example 43

(2S,4R)—N-(1-cyanocyclopropyl)-4-(2'-(hydroxymethyl)biphenyl-4-ylsulfonyl)-1-(1-(trifluoromethyl)cyclopropanecarbonyl)pyrrolidine-2-carboxamide

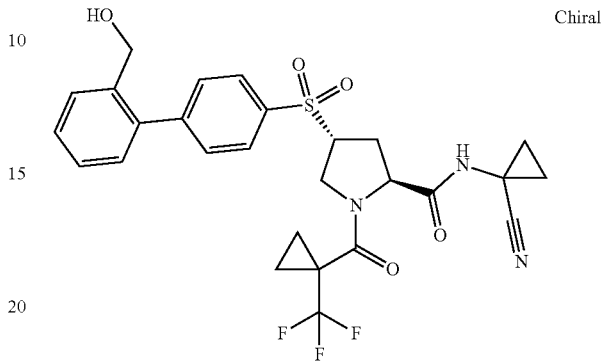

To a solution of (2S,4R)—N-(1-cyanocyclopropyl)-4-(2'-formylbiphenyl-4-ylsulfonyl)-1-(1-(trifluoromethyl)cyclopropanecarbonyl)pyrrolidine-2-carboxamide (example 37, 35.6 mg, 63.6 µmol) in methanol (1 mL) was added under stirring and under an atmosphere of nitrogen sodium borohydride (2.41 mg, 63.6 µmol). The reaction was stirred at room temperature over night. Water was added and the reaction was extracted twice with ethyl acetate. The organic layer was washed with saturated aqueous sodium chloride solution, dried over sodium sulfate, filtered and the solvent was removed under reduced pressure. The residue was stirred with heptane for 15 minutes, filtered and dried to yield the title compound as a white powder (26.4 mg, 74%). m/z=560.2 [M−H]−.

Example 44

(2S,4R)-4-(4-(2-aminopyrimidin-5-yl)-2-methylphenylsulfonyl)-N-(1-cyanocyclopropyl)-1-(1-(trifluoromethyl)cyclopropanecarbonyl)pyrrolidine-2-carboxamide

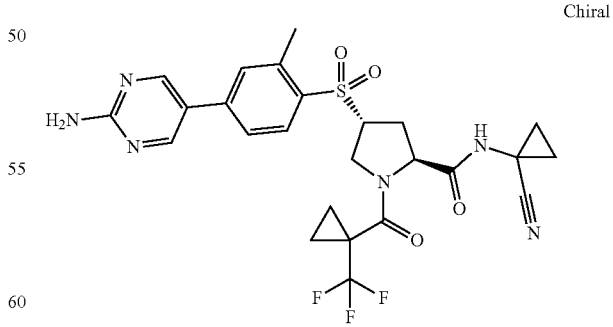

The title compound was prepared in analogy to example 20, step c) from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 2-aminopyrimidin-5-ylboronic acid and obtained as a off-white solid (78.8 mg, 70%) after purification on preparative HPLC. m/z=563.4 [M+H]+.

Example 45

(2S,4R)-4-[4-(2,2-Difluoro-benzo[1,3]dioxol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

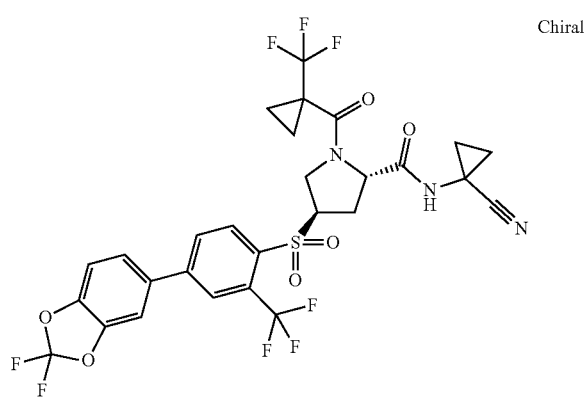 [SMILES: N#CC1(NC(=O)[C@@H]2C[C@@H](S(=O)(=O)c3ccc(-c4ccc5c(c4)OC(F)(F)O5)cc3C(F)(F)F)CN2C(=O)C2(C(F)(F)F)CC2)CC1]

Example 3f) (100 mg, 166 µmol, Eq: 1.00), 2,2-difluorobenzo[d][1,3]dioxol-5-ylboronic acid (50.3 mg, 249 µmol, Eq: 1.50) were dissolved in dioxane (2 mL). Aqueous 2M Na₂CO₃ solution (415 µl, 830 µmol, Eq: 5.00) and 1,1'-bis(diphenylphosphino)-ferrocenepalladium(II) dichloride dichloromethane complex (6.78 mg, 8.3 µmol, Eq: 0.05) were added to the solution and stirred at 85° C. for 13 h. The crude material was filtered and purified by preparative HPLC to yield the title compound as light yellow foam (83 mg; 74%). m/z=680.2 [M+H]+.

Example 46

(2S,4R)-1-(1-Trifluoromethyl-cyclopropanecarbonyl)-4-[2-trifluoromethyl-4-(4-trifluoromethyl-pyrazol-1-yl)-benzenesulfonyl]-pyrrolidine-2-carboxylic acid (1-cyano-cyclopropyl)-amide

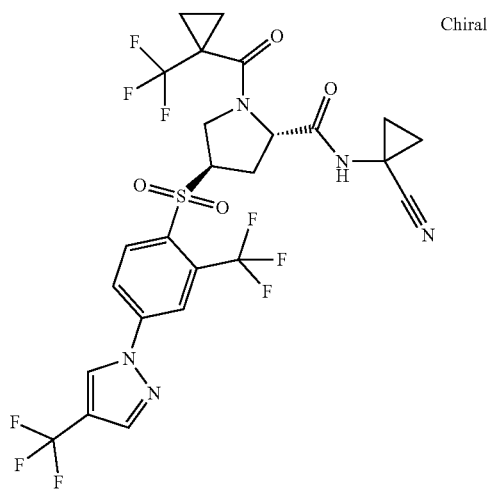 [SMILES: N#CC1(NC(=O)[C@@H]2C[C@@H](S(=O)(=O)c3ccc(-n4cc(C(F)(F)F)cn4)cc3C(F)(F)F)CN2C(=O)C2(C(F)(F)F)CC2)CC1]

Example 46 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 4-(trifluoromethyl)-1H-pyrazole by stirring the reaction mixture at 22° C. for 24 h to yield the title compound as a colorless foam (75 mg; 62%). m/z=657.1103 [M+H]+.

Example 47

(2S,4R)-4-[4-(5-Methyl-tetrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

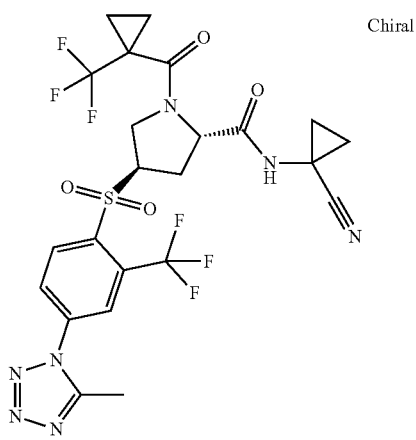 [SMILES: Cc1nnnn1-c1ccc(S(=O)(=O)[C@@H]2C[C@@H](C(=O)NC3(C#N)CC3)N(C(=O)C3(C(F)(F)F)CC3)C2)c(C(F)(F)F)c1]

Example 47 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 5-methyl-1H-tetrazole by stirring the reaction mixture at 22° C. for 24 h to yield the title compound as a colorless amorphous solid (63 mg; 28%). m/z=605.1289 [M+H]+.

Example 48

(2S,4R)-4-[4-(2,4-Dimethyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

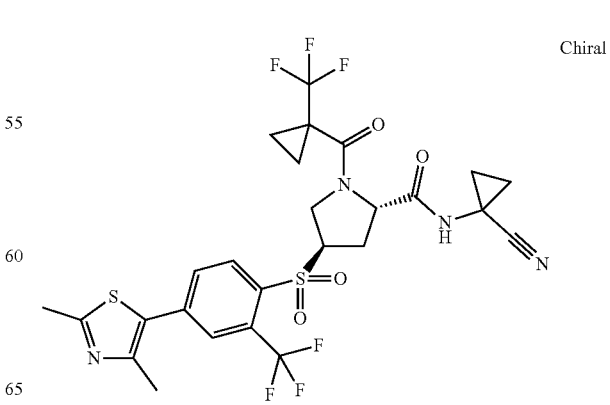

In a 5 mL microwavetube, example 3f) (100 mg, 166 μmol, Eq: 1.00), potassium acetate (24.4 mg, 249 μmol, Eq: 1.50) and tetrakis(triphenylphosphine)palladium (0) (9.59 mg, 8.3 μmol, Eq: 0.05) were dissolved in DMA (1 mL). Now 2,4-dimethylthiazole (94.0 mg, 89.0 μl, 830 μmol, Eq: 5.00) was added. The tube was sealed and the mixture was stirred for 30 min at 170° C. in the microwave oven. After that, 2,4-dimethylthiazole (94.0 mg, 89.0 μl, 830 μmol, Eq: 5.00) was added to the reaction mixture. The reaction mixture was heated in the microwave oven at 170° C. for 30 min. Now, the reaction mixture was poured into EtOAc (15 mL) and extracted with 0.1M aqueous HCl solution (20 mL). The aqueous layer was back-extracted with EtOAc (2×15 mL). The organic layers were combined, then dried over Na$_2$SO$_4$, filtered and concentrated in vacuo. The crude material was purified by flash chromatography (silica gel, 4 g, 0% to 60% EtOAc in DCM). The roughly purified material was in addition purified by preparative HPLC to yield the title compound as a colorless solid (11 mg; 10%). m/z=635.1210 [M+H]$^+$.

Example 49

(2S,4R)—N-(1-cyanocyclopropyl)-4-(4-(2,4-dimethylthiazol-5-yl)phenylsulfonyl)-1-(1-(trifluoromethyl)cyclopropanecarbonyl)pyrrolidine-2-carboxamide

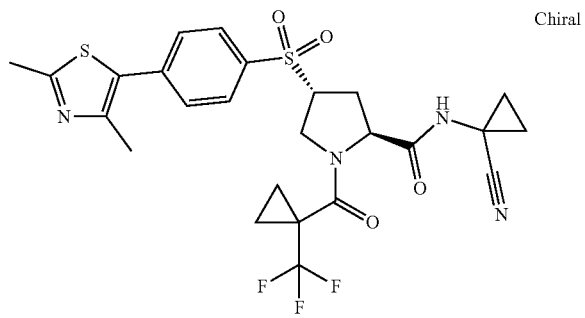 [SMILES: Cc1nc(C)c(-c2ccc(S(=O)(=O)[C@@H]3C[C@@H](C(=O)NC4(C#N)CC4)N(C(=O)C4(C(F)(F)F)CC4)C3)cc2)s1]

Example 49 was prepared in analogy to example 48 starting from (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b) and 2,4-dimethylthiazole to yield the title compound as a white powder (44 mg, 39%) after purification on preparative HPLC. m/z=565.2 [M−H]$^−$.

Example 50

(2S,4R)—N-(1-cyanocyclopropyl)-4-(4-(2-methylthiazol-5-yl)phenylsulfonyl)-1-(1-(trifluoromethyl)cyclopropanecarbonyl)pyrrolidine-2-carboxamide

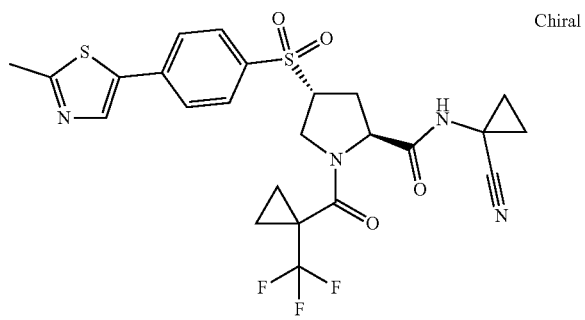 [SMILES: Cc1ncc(-c2ccc(S(=O)(=O)[C@@H]3C[C@@H](C(=O)NC4(C#N)CC4)N(C(=O)C4(C(F)(F)F)CC4)C3)cc2)s1]

Example 50 was prepared in analogy to example 48 starting from (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b) and 2-methylthiazole to yield the title compound as a white powder (42 mg, 38%) after purification on preparative HPLC. m/z=551.3 [M−H]$^−$.

Example 51

(2S,4R)—N-(1-cyanocyclopropyl)-4-(4-(2-methoxypyrimidin-5-yl)phenylsulfonyl)-1-(1-(trifluoromethyl)cyclopropanecarbonyl)pyrrolidine-2-carboxamide

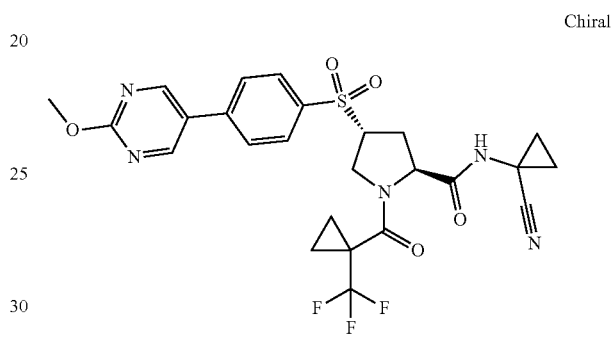

The title compound was prepared in analogy to example 20, step c) from (2S,4R)-4-(4-bromo-phenylsulfonyl)-N-(1-cyanocyclopropyl)-1-(1-(trifluoromethyl)cyclopropanecarbonyl)pyrrolidine-2-carboxamide (example 20b) and 2-methoxypyrimidin-5-ylboronic acid and obtained as a white powder (67.2 mg, 60%). m/z=562.1 [M−H]$^−$.

Example 52

(2S,4R)-4-(2-chloro-4-(5-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide

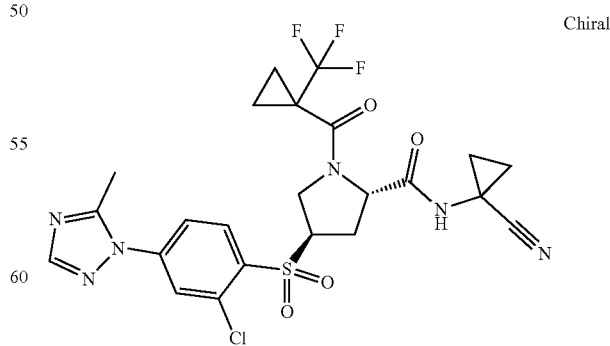

Example 52 was obtained as a regioisomer during the synthesis of example 14 to yield the title compound as a white solid (69 mg; 15%). m/z=571.2 [M+H]$^+$.

Example 53

(2S,4R)-4-(4-[1,2,3]Triazol-2-yl-2-trifluoromethyl-benzenesulfonyl)-1-(1-trifluoromethyl-cyclopropanecarbonyl)-pyrrolidine-2-carboxylic acid (1-cyano-cyclopropyl)-amide

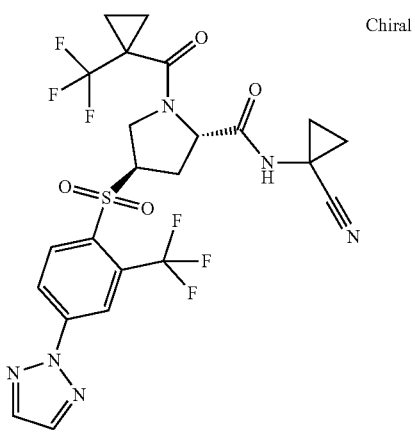 [SMILES: N#CC1(NC(=O)[C@@H]2C[C@@H](S(=O)(=O)c3ccc(-n4nccn4)cc3C(F)(F)F)CN2C(=O)C2(C(F)(F)F)CC2)CC1]

Example 53 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 1H-1,2,3-triazole by stirring the reaction mixture at 22° C. for 24 h to yield the title compound as a colorless foam (89 mg; 41%). m/z=590.1175 [M+H]$^+$.

Example 54

(2S,4R)-4-(4-[1,2,3]Triazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide

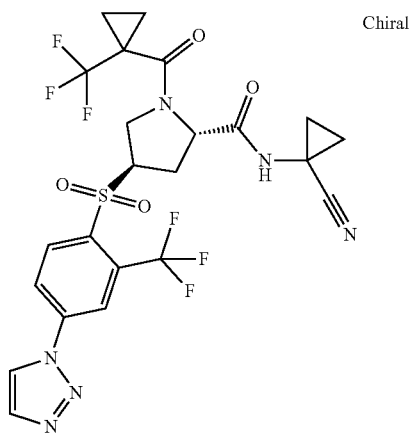 [SMILES: N#CC1(NC(=O)[C@@H]2C[C@@H](S(=O)(=O)c3ccc(-n4ccnn4)cc3C(F)(F)F)CN2C(=O)C2(C(F)(F)F)CC2)CC1]

Example 54 was obtained as regioisomer during the synthesis of example 53 to yield the title compound as a colorless foam (38 mg; 36%). m/z=590.1175 [M+H]$^+$.

Example 55

(2S,4R)—N-(1-cyanocyclopropyl)-4-(4-(3,5-dimethylisoxazol-4-yl)phenylsulfonyl)-1-(1-(trifluoromethyl)cyclopropanecarbonyl)pyrrolidine-2-carboxamide

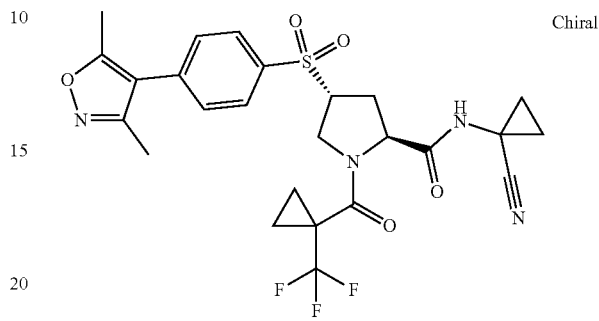

Example 55 was prepared in analogy to example 48 starting from (2S,4R)-4-(4-bromophenylsulfonyl)-N-(1-cyanocyclopropyl)-1-(1-(trifluoromethyl)cyclopropanecarbonyl)pyrrolidine-2-carboxamide (example 20b) and 3,5-dimethylisoxazole to yield the title compound as a colorless solid (10 mg, 9%) after purification on preparative HPLC. m/z=549.2 [M−H]$^-$.

Example 56

(2S,4R)-4-[4-(1-Difluoromethyl-1Hpyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

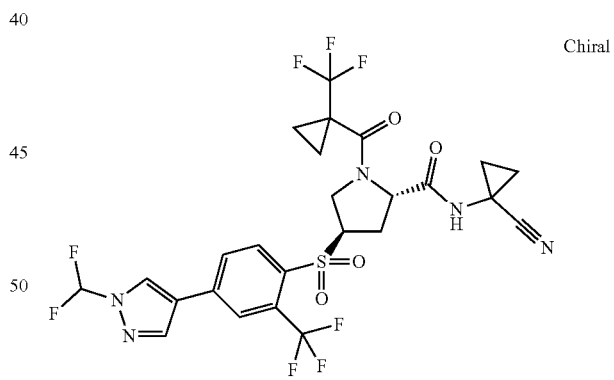

Example 3f) (100 mg, 166 μmol, Eq: 1.00), 1-(difluoromethyl)-4-(4,4,5,5-tetramethyl-1,3,2-dioxaborolan-2-yl)-1H-pyrazole (60.8 mg, 249 μmol, Eq: 1.50) were dissolved in dioxane (2 mL). Aqueous 2M Na$_2$CO$_3$ solution (415 μl, 830 μmol, Eq: 5.00) and 1,1'-bis (diphenylphosphino)ferrocene.palladium(II) dichloride dichloromethane complex (6.78 mg, 8.3 μmol, Eq: 0.05) were added to the solution and stirred at 85° C. for 14 h. The crude material was filtered and purified by preparative HPLC. After that, the material was purified by flash chromatography (silica gel, 4 g, 0% to 66% EtOAc in heptane) to yield the title compound as light yellow foam (90 mg; 85%). m/z=638.1113 [M−H]$^-$.

Example 57

(2S,4R)-4-[4-(5-Methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

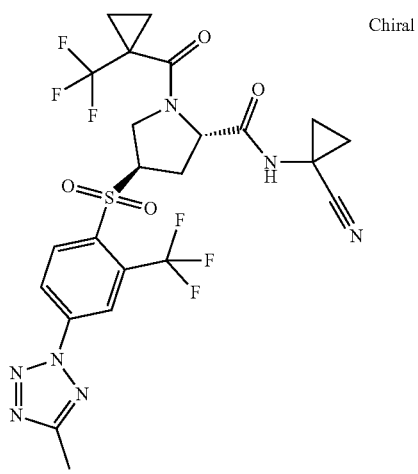 [SMILES: Cc1nnn(-c2ccc(S(=O)(=O)[C@@H]3C[C@@H](C(=O)NC4(C#N)CC4)N(C(=O)C4(C(F)(F)F)CC4)C3)c(C(F)(F)F)c2)n1]

Example 57 was obtained as a regioisomer during the synthesis of example 47 to yield the title compound as a colorless amorphous solid (34 mg; 15%). m/z=604.2 [M–H]⁻.

Example 58

(2S,4R)-1-(1-Trifluoromethyl-cyclopropanecarbonyl)-4-[2-trifluoromethyl-4-(3-trifluoromethyl-1Hpyrazol-4-yl)-benzenesulfonyl]-pyrrolidine-2-carboxylic acid (1-cyano-cyclopropyl)-amide

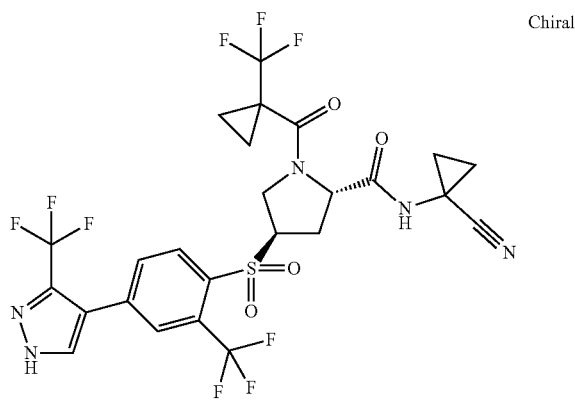 [SMILES: N#CC1(NC(=O)[C@@H]2C[C@@H](S(=O)(=O)c3ccc(-c4c[nH]nc4C(F)(F)F)cc3C(F)(F)F)CN2C(=O)C2(C(F)(F)F)CC2)CC1]

Example 58 was prepared in analogy to example 56 starting from example 3f) and 4-(4,4,5,5-tetramethyl-1,3,2-dioxaborolan-2-yl)-3-(trifluoromethyl)-1H-pyrazole to yield the title compound as a white solid (6.0 mg; 5.5%). m/z=658.5 [M+H]⁺.

Example 59

(2S,4R)—N-(1-cyanocyclopropyl)-4-(2'-(hydroxymethyl)-3-methylbiphenyl-4-ylsulfonyl)-1-(1-(trifluoromethyl)cyclopropanecarbonyl)pyrrolidine-2-carboxamide

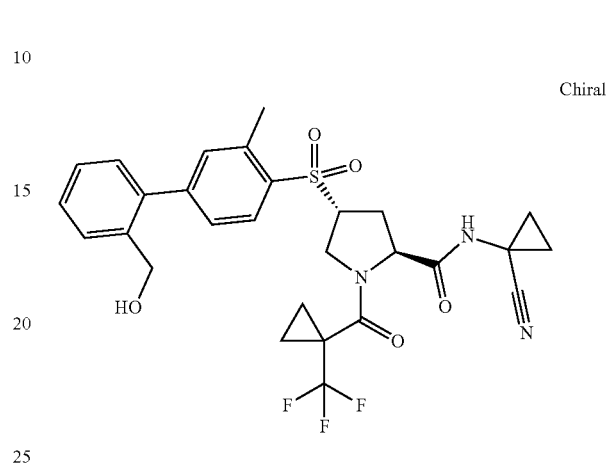

Example 59 was prepared in analogy to example 43 starting from (2S,4R)—N-(1-cyanocyclopropyl)-4-(2'-formyl-3-methylbiphenyl-4-ylsulfonyl)-1-(1-(trifluoromethyl)cyclopropanecarbonyl)pyrrolidine-2-carboxamide (example 29) to yield the title compound as a off-white solid (36.1 mg, 45%) after purification on preparative HPLC. m/z=574.2 [M–H]⁻.

Example 60

(2S,4R)—N-(1-cyanocyclopropyl)-4-(4-(2,4-dimethylthiazol-5-yl)-2-methylphenylsulfonyl)-1-(1-(trifluoromethyl)cyclopropanecarbonyl)pyrrolidine-2-carboxamide

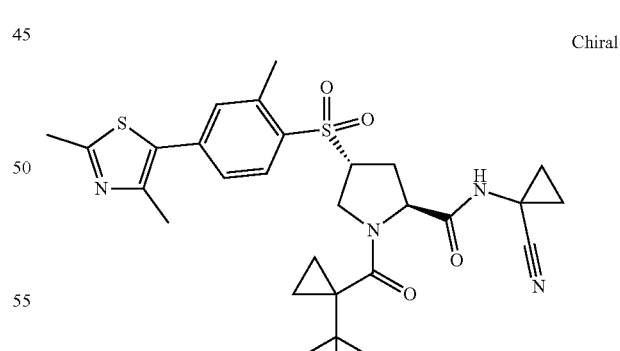

Example 60 was prepared in analogy to example 48 starting from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 2,4-dimethylthiazole to yield the title compound as a off-white solid (44.9 mg, 39%) after purification on preparative HPLC. m/z=581.2 [M+H]⁺.

Example 61

(2S,4R)—N-(1-cyanocyclopropyl)-4-(2-methyl-4-(2-methylthiazol-5-yl)phenylsulfonyl)-1-(1-(trifluoromethyl)cyclopropanecarbonyl)pyrrolidine-2-carboxamide

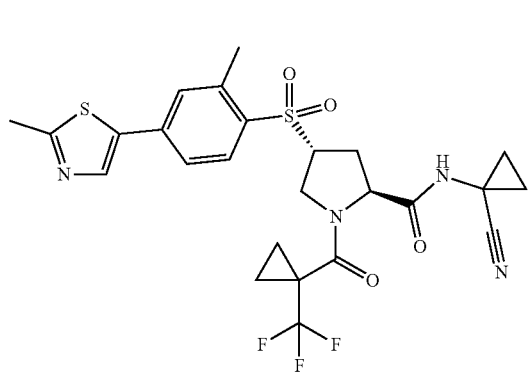

Example 61 was prepared in analogy to example 48 starting from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 2-methylthiazole to yield the title compound as a off-white solid (55.9 mg, 49%) after purification on preparative HPLC. m/z=567.2 [M+H]$^+$.

Example 62

(2S,4R)—N-(1-cyanocyclopropyl)-4-(4-(2-methoxypyrimidin-5-yl)-2-methylphenylsulfonyl)-1-(1-(trifluoromethyl)cyclopropanecarbonyl)pyrrolidine-2-carboxamide

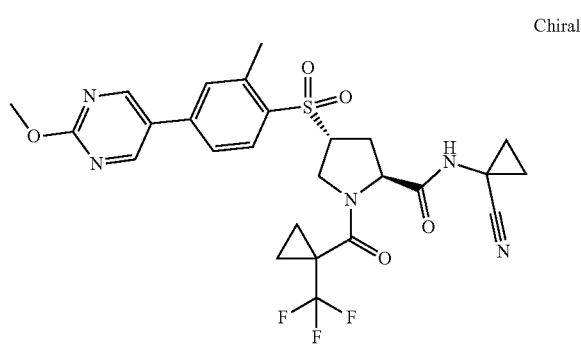 [SMILES: COc1ncc(-c2ccc(S(=O)(=O)[C@@H]3C[C@@H](C(=O)NC4(C#N)CC4)N(C(=O)C4(C(F)(F)F)CC4)C3)c(C)c2)cn1]

The title compound was prepared in analogy to example 20, step c) from (2S,4R)-4-(4-bromo-2-methylphenylsulfonyl)-N-(1-cyanocyclopropyl)-1-(1-(trifluoromethyl)cyclopropanecarbonyl)pyrrolidine-2-carboxamide (example 22b) and 2-methoxypyrimidin-5-ylboronic acid and obtained as a light brown solid (72 mg, 62%). m/z=578.2 [M+H$^+$].

Example 63

(2S,4R)-4-[4-(2-Methyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

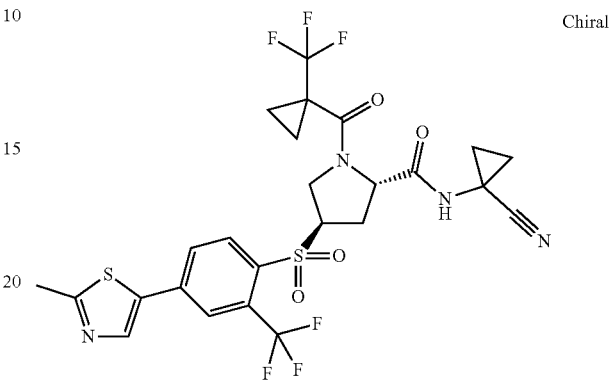

In a 5 mL microwavetube, example 3f) (100 mg, 166 μmol, Eq: 1.00), potassium acetate (24.4 mg, 249 μmol, Eq: 1.50) and tetrakis(triphenylphosphine)palladium (0) (9.59 mg, 8.3 mol, Eq: 0.05) were combined with DMA (1 mL). 2-Methylthiazole (82.3 mg, 74.2 μl, 830 μmol, Eq: 5.00) was added. The tube was sealed and the mixture was stirred for 30 minutes at 160° C. in the microwave oven. The reaction mixture was poured into EtOAc (15 mL) and extracted with 0.1 M aqueous HCl solution (1×20 mL). The aqueous layer was back-extracted with EtOAc (2×10 mL). The organic layers were dried over Na$_2$SO$_4$ and concentrated in vacuo. The crude material was purified by flash chromatography (silica gel, 4 g, 0% to 60% EtOAc in DCM) to yield the title compound as an off-white solid (8 mg; 8%). m/z=621.1064 [M+H]$^+$.

Example 64

(2S,4R)—N-(1-cyanocyclopropyl)-4-(4-(3,5-dimethylisoxazol-4-yl)-2-methylphenylsulfonyl)-1-(1-(trifluoromethyl)cyclopropanecarbonyl)pyrrolidine-2-carboxamide

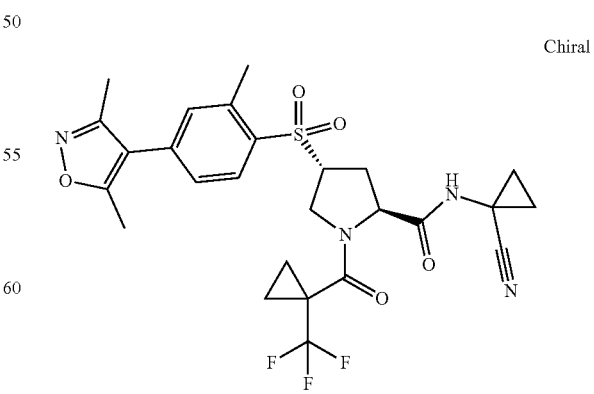

Example 64 was prepared in analogy to example 48 starting from (2S,4R)-4-(4-bromophenylsulfonyl)-N-(1- cyanocyclopropyl)-1-(1-(trifluoromethyl)cyclopropanecarbonyl)pyrrolidine-2-carboxamide (example 20b) and 3,5-dimethylisoxazole to yield the title compound as a off-white solid (28.5 mg, 25%) after purification on preparative HPLC. m/z=565.3 [M+H]+.

Example 65

(2S,4R)-4-(4-Tetrazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide

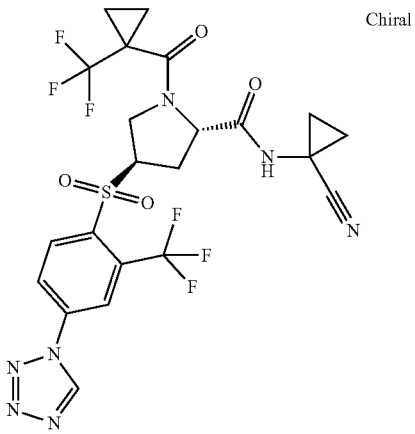 [SMILES: N#CC1(NC(=O)[C@@H]2C[C@@H](S(=O)(=O)c3ccc(-n4cnnn4)cc3C(F)(F)F)CN2C(=O)C2(C(F)(F)F)CC2)CC1]

Example 65 was prepared in analogy to example 10 starting from (2S,4R)-4-(4-fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide (example 7b)) and 1H-tetrazole by stirring the reaction mixture at 22° C. for 48 h to yield the title compound as an amorphous colorless solid (29 mg; 13%). m/z=591.113 [M+H]+.

Example 66

(2S,4R)-4-(4-(3-chloro-1H-1,2,4-triazol-1-yl)-2-methylphenylsulfonyl)-N-(1-cyanocyclopropyl)-1-(1-(trifluoromethyl)cyclopropanecarbonyl)pyrrolidine-2-carboxamide

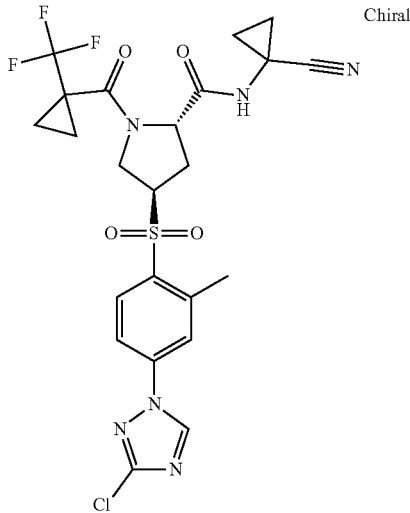 [SMILES: Cc1cc(-n2cnc(Cl)n2)ccc1S(=O)(=O)[C@@H]1C[C@@H](C(=O)NC2(C#N)CC2)N(C(=O)C2(C(F)(F)F)CC2)C1]

Under an atmosphere of argon, (2S,4R)—N-(1-cyanocyclopropyl)-4-(4-fluoro-2-methylphenylsulfonyl)-1-(1-(trifluoromethyl)cyclopropanecarbonyl)pyrrolidine-2-carboxamide (example 19, step b, 0.2 g, 410 µmol) was combined with N,N-dimethylacetamide (8.00 mL) to give a colorless suspension. 3-Chloro-1H-1,2,4-triazole (86.7 mg, 821 µmol) and cesium carbonate (267 mg, 821 µmol) were added. The reaction mixture was stirred over 5 days and was subsequently heated to 140° C. for 30 min in a microwave oven. The reaction mixture was then poured into water (40 mL) and extracted with ethyl acetate (2×40 mL). The crude material was purified by preparative HPLC and obtained as a light yellow, viscous oil (12 mg, 5.1%). m/z=571.11 [M+H+].

Example 67

(2R,4R)-4-(4-(3-chloro-1H-1,2,4-triazol-1-yl)-2-methylphenylsulfonyl)-N-(1-cyanocyclopropyl)-1-(1-(trifluoromethyl)cyclopropanecarbonyl)pyrrolidine-2-carboxamide

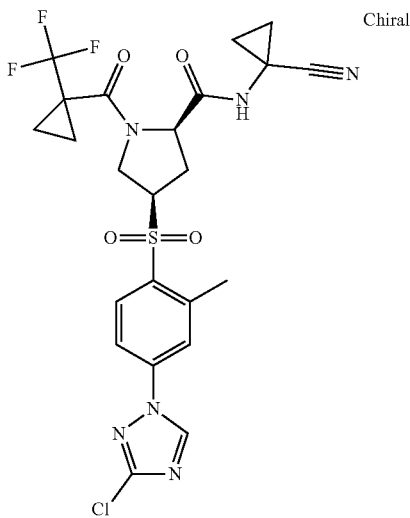 [SMILES: Cc1cc(-n2cnc(Cl)n2)ccc1S(=O)(=O)[C@@H]1C[C@H](C(=O)NC2(C#N)CC2)N(C(=O)C2(C(F)(F)F)CC2)C1]

The title compound was obtained as a by-product in the preparation of example 66 and was obtained as a light yellow viscous oil (13.9 mg, 5.9%, stereochemistry assigned by NOESY-NMR). m/z=571.1137 [M+H+].

Example 68

(2S,4R)-4-[4-(1-Methyl-3-trifluoromethyl-1Hpyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

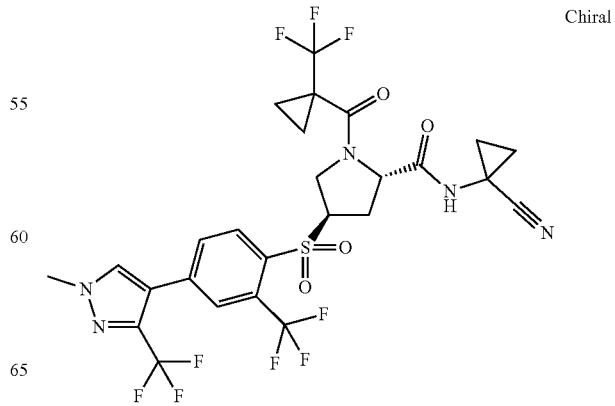

Example 68 was prepared in analogy to example 56 starting from example 3f) and 1-methyl-4-(4,4,5,5-tetramethyl-1,3,2-dioxaborolan-(trifluoromethyl)-1H-pyrazole to yield the title compound as a white foam (167 mg; 75%). m/z=689.1581 [M+NH$_4$]$^+$.

Example 69

(2S,4R)-4-(4-(3-chloro-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide

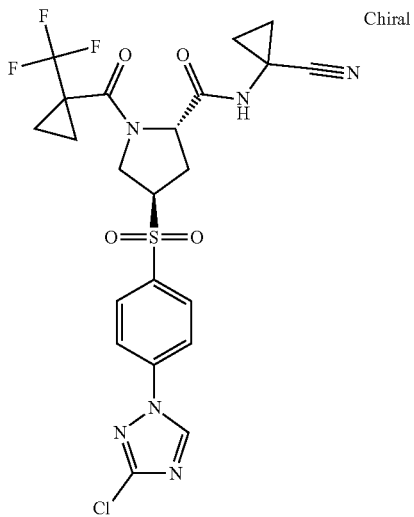 [SMILES: N#CC1(NC(=O)[C@@H]2C[C@@H](S(=O)(=O)c3ccc(-n4cnc(Cl)n4)cc3)CN2C(=O)C2(C(F)(F)F)CC2)CC1]

Under an atmosphere of argon, (2S,4R)—N-(1-cyanocyclopropyl)-4-(4-fluorophenylsulfonyl)-1-(1-(trifluoromethyl)cyclopropanecarbonyl)pyrrolidine-2-carboxamide (example 33, step b, 0.3 g, 634 µmol) was combined with N,N-dimethylacetamide (12 mL) to give a colorless suspension. 3-Chloro-1H-1,2,4-triazole (134 mg, 1.27 mmol) and cesium carbonate (413 mg, 1.27 mmol, Eq: 2) were added. The reaction mixture was stirred over the weekend at ambient temperature, and was subsequently heated to 140° C. for 30 min in a microwave oven. The reaction mixture was poured into water (50 mL) and extracted with ethyl acetate (2×50 mL). The crude material was purified by preparative HPLC to yield the title compound as a colorless viscous oil (93.9 mg, 26.6%). m/z=557.09 [M+H$^+$].

Example 70

Cathepsin Enzyme Inhibition Assay

Enzyme activity is measured by observing the increase in fluorescence intensity caused by cleavage of a peptide substrate containing a fluorophore whose emission is quenched in the intact peptide.
Assay buffer: 100 mM potassium phosphate pH 6.5, EDTA-Na 5 mM, Triton X-100 0.001%, DTT 5 mM.
Enzymes (all at 1 nM): human and mouse Cathepsin S, Cat K, Cat B, Cat L.
Substrate (20 µM): Z-Val-Val-Arg-AMC, except for Cat K which uses Z-Leu-Arg-AMC (both from Bachem).
Z=Benzyloxycarbonyl.
AMC=7-Amino-4-Methyl-Coumarin.
DTT=dithiothreitol.
Final volume: 100 µL.
Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. IC$_{50}$ are calculated by standard methods.

Inhibition of human Cat S, mouse Cat S, human Cat K, human Cat B, human Cat L and mouse Cat L have been measured separately. The results obtained for human Cat S for representative compounds of the invention are expressed in the following table in µM.

| Example | IC$_{50}$ |
| --- | --- |
| 1 | 0.000968 |
| 2 | 0.00077 |
| 3 | 0.001018 |
| 4 | 0.000978 |
| 5 | 0.000836 |
| 6 | 0.001062 |
| 7 | 0.00091 |
| 8 | 0.000533 |
| 9 | 0.000683 |
| 10 | 0.000686 |
| 11 | 0.012625 |
| 12 | 0.00056 |
| 13 | 0.000568 |
| 14 | 0.000529 |
| 15 | 0.00061 |
| 16 | 0.000563 |
| 17 | 0.000704 |
| 18 | 0.00098 |
| 19 | 0.001431 |
| 20 | 0.005716 |
| 21 | 0.001071 |
| 22 | 0.001136 |
| 23 | 0.001123 |
| 24 | 0.000772 |
| 25 | 0.00327 |
| 26 | 0.000391 |
| 27 | 0.000558 |
| 28 | 0.00233 |
| 29 | 0.000811 |
| 30 | 0.000625 |
| 31 | 0.00054 |
| 32 | 0.000955 |
| 33 | 0.001568 |
| 34 | 0.001062 |
| 35 | 0.00102 |
| 36 | 0.002597 |
| 37 | 0.001894 |
| 38 | 0.003208 |
| 39 | 0.000483 |
| 40 | 0.001208 |
| 41 | 0.00086 |
| 42 | 0.001458 |
| 43 | 0.003572 |
| 44 | 0.00051 |
| 45 | 0.00107 |
| 46 | 0.000752 |
| 47 | 0.000349 |
| 48 | 0.001167 |
| 49 | 0.000909 |
| 50 | 0.000728 |
| 51 | 0.000882 |
| 52 | 0.000486 |
| 53 | 0.000506 |
| 54 | 0.000382 |
| 55 | 0.001436 |
| 56 | 0.000526 |
| 57 | 0.000564 |
| 58 | 0.002421 |
| 59 | 0.000943 |
| 60 | 0.000614 |
| 61 | 0.000613 |
| 62 | 0.000592 |
| 63 | 0.000585 |

-continued

| Example | IC$_{50}$ |
|---|---|
| 64 | 0.00065 |
| 65 | 0.000584 |
| 66 | 0.2227 |
| 67 | 0.54225 |
| 68 | 0.000829 |
| 69 | 0.49675 |

The compounds of the invention are preferential inhibitors of Cathepsin-S over Cathepsin-L, K and B.

The compounds according to the invention have, in the foregoing assay, an IC$_{50}$ at Cat S which is between 0.00001 and 100 µM, in particular between 0.00001 and 50 µM, more particularly between 0.00001 and 20 M. The particular compounds of the invention have an IC$_{50}$ in the foregoing assay below 0.09 µM.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

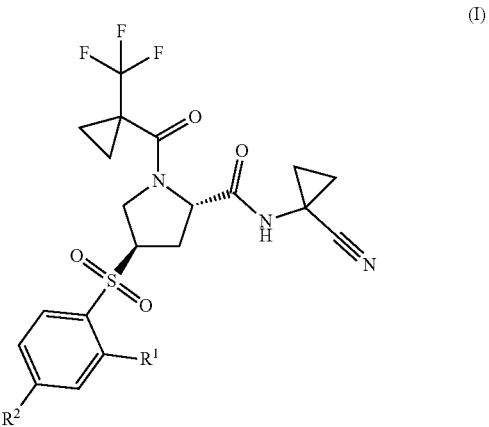

(I)

or a pharmaceutically acceptable salt or ester thereof, wherein
    $R^1$ is selected from the group consisting of hydrogen, alkyl, haloalkyl, halogen and triazolyl; and
    $R^2$ is selected from the group consisting of (halo)(oxy)pyridinyl, (alkyl)(oxy)pyridinyl, (alkyl)(haloalkyl)pyrazolyl, haloalkoxyphenyl, alkoxyphenyl, cycloalkyloxyphenyl, cycloalkyloxy, alkyltetrazolyl, triazolyl, alkyltriazolyl, dialkyltriazolyl, halotriazolyl, haloalkylpyrazolyl, formylphenyl, aminopyrimidinyl, cyanophenyl, (alkoxy)(dihalo)phenyl, hydroxyalkylphenyl, benzo[1,3]dioxolyl, dialkylthiazolyl, alkylthiazolyl, alkoxypyrimidinyl, dialkylisoxazolyl and (halo)(haloalkyl)triazolyl.

2. A compound according to claim 1, or a pharmaceutically acceptable salt or ester thereof, wherein $R^1$ is alkyl, haloalkyl or halogen.

3. A compound according to claim 1, or a pharmaceutically acceptable salt of ester there, wherein $R^1$ is methyl, trifluoromethyl or chlorine.

4. A compound according to claim 1, or a pharmaceutically acceptable salt or ester thereof, wherein $R^2$ is selected from the group consisting of (alkyl)(haloalkyl)pyrazolyl, alkyltetrazolyl, triazolyl, alkyltriazolyl, dialkyltriazolyl, halotriazolyl, haloalkylpyrazolyl, dialkylthiazolyl, alkylthiazolyl and dialkylisoxazolyl.

5. A compound according to claim 1, or a pharmaceutically acceptable salt or ester thereof, wherein $R^2$ is selected from the group consisting of (methyl)(trifluoromethyl)pyrazolyl, methyltetrazolyl, triazolyl, methyltriazolyl, dimethyltriazolyl, chlorotriazolyl, trifluoromethylpyrazolyl, difluoromethylpyrazolyl, dimethylthiazolyl, methylthiazolyl and dimethylisoxazolyl.

6. A compound according to claim 1, selected from
(2S,4R)-4-[4-(2-Chloro-1-oxy-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(2-Methyl-1-oxy-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(2-Methyl-5-trifluoromethyl-2H-pyrazol-3-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-(2'-Trifluoromethoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;
(2S,4R)-4-(2'-Ethoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;
(2S,4R)-4-(2'-Cyclopropoxy-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;
(2S,4R)-4-(4-Cyclobutoxy-2-trifluoromethyl-benzenesulfonyl)-1-(1-trifluoromethyl-cyclopropanecarbonyl)-pyrrolidine-2-carboxylic acid (1-cyano-cyclopropyl)-amide;
(2S,4R)-4-(2-chloro-4-(5-methyl-2H-tetrazol-2-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(5-methyl-1H-tetrazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(1H-1,2,4-triazol-1-yl)phenyl sulfonyl)-N-(1-cyanocyclopropyl)-1-(1-(trifluoromethyl) cyclopropanecarbonyl)pyrrolidine-2-carboxamide;
(2S,4R)—N-(1-cyanocyclopropyl)-4-(2,4-di(1H-1,2,4-triazol-1-yl)phenyl sulfonyl)-1-(1-(trifluoromethyl)cyclopropanecarbonyl)pyrrolidine-2-carboxamide;
(2S,4R)-4-(2-chloro-4-(2H-1,2,3-triazol-2-yl)phenyl sulfonyl)-N-(1-cyanocyclopropyl)-1-(1-(trifluoromethyl) cyclopropanecarbonyl)pyrrolidine-2-carboxamide;
(2S,4R)-4-(2-chloro-4-(1H-1,2,3-triazol-1-yl)phenyl sulfonyl)-N-(1-cyanocyclopropyl)-1-(1-(trifluoromethyl) cyclopropanecarbonyl)pyrrolidine-2-carboxamide;
(2S,4R)-4-(2-chloro-4-(3-methyl-1H-1,2,4-triazol-1-yl) phenylsulfonyl)-N-(1-cyanocyclopropyl)-1-(1-(trifluoromethyl)cyclopropanecarbonyl)pyrrolidine-2-carboxamide;
(2S,4R)-4-(2-chloro-4-(3,5-dimethyl-1H-1,2,4-triazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(3-chloro-1H-1,2,4-triazol-1-yl) phenylsulfonyl)-N-(1-cyanocyclopropyl)-1-(1-(trifluoromethyl)cyclopropanecarbonyl)pyrrolidine-2-carboxamide;
(2S,4R)-4-(2-chloro-4-(3-(trifluoromethyl)-1H-pyrazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(5-methyl-3-(trifluoromethyl)-1H-pyrazol-1-yl)phenyl sulfonyl)-N-(1-cyanocyclopropyl)-1-(1-(trifluoromethyl)cyclopropanecarbonyl)pyrrolidine-2-carboxamide;
(2S,4R)—N-(1-cyanocyclopropyl)-4-(2-methyl-4-(3-(trifluoromethyl)-1H-pyrazol-1-yl)phenyl sulfonyl)-1-(1-(trifluoromethyl)cyclopropanecarbonyl)pyrrolidine-2-carboxamide;
(2S,4R)—N-(1-cyanocyclopropyl)-4-(2'-(trifluoromethoxy)biphenyl-4-ylsulfonyl)-1-(1-(trifluoromethyl)cyclopropanecarbonyl)pyrrolidine-2-carboxamide;
(2S,4R)-4-(2-chloro-4-cyclobutoxyphenylsulfonyl)-N-(1-cyanocyclopropyl)-1-(1-(trifluoromethyl)cyclopropanecarbonyl)pyrrolidine-2-carboxamide;
(2S,4R)—N-(1-cyanocyclopropyl)-4-(3-methyl-2'-(trifluoromethoxy)biphenyl-4-yl sulfonyl)-1-(1-(trifluoromethyl)cyclopropanecarbonyl)pyrrolidine-2-carboxamide;
(2S,4R)-4-[4-(5-Methyl-3-trifluoromethyl-pyrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(3-Methyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(3-Methyl-[1,2,4]triazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-(4-(1H-1,2,4-triazol-1-yl)-2-(trifluoromethyl) phenyl sulfonyl)-N-(1-cyanocyclopropyl)-1-(1-(trifluoromethyl)cyclopropanecarbonyl)pyrrolidine-2-carboxamide (2S,4R)-4-[4-(3,5-Dimethyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)—N-(1-cyanocyclopropyl)-4-(5-methyl-1H-1,2,4-triazol-1-yl)-2-(trifluoromethyl)phenyl sulfonyl)-1 (1-trifluoromethyl)cyclopropanecarbonyl)pyrrolidine-2-carboxamide;
(2S,4R)-4-[4-(3-Chloro-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)—N-(1-cyanocyclopropyl)-4-(4-(5-methyl-1H-1,2,4-triazol-1-yl)-2-(trifluoromethyl)phenyl sulfonyl)-1-(1-(trifluoromethyl) cyclopropanecarbonyl)pyrrolidine-2-carboxamide;
(2S,4R)—N-(1-cyanocyclopropyl)-4-(2-methyl-4-(1-methyl-3-(trifluoromethyl)-1H-pyrazol-5-yl)phenyl sulfonyl)-1-(1-(trifluoromethyl)cyclopropanecarbonyl) pyrrolidine-2-carboxamide;
(2S,4R)—N-(1-cyanocyclopropyl)-4-(4-(3,5-dimethyl-1H-1,2,4-triazol-1-yl)phenyl sulfonyl)-1-(1-(trifluoromethyl)cyclopropanecarbonyl)pyrrolidine-2-carboxamide;
(2S,4R)-4-(4-(1H-1,2,3-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(4-(3-(trifluoromethyl)-1H-pyrazol-1-yl)phenylsulfonyl)-1-(1-(trifluoromethyl)cyclopropanecarbonyl)pyrrolidine-2-carboxamide;

(2S,4R)—N-(1-cyanocyclopropyl)-4-(4-(5-methyl-3-(trifluoromethyl)-1H-pyrazol-1-yl)phenylsulfonyl)-1-(1-(trifluoromethyl)cyclopropanecarbonyl)pyrrolidine-2-carboxamide;

(2S,4R)—N-(1-cyanocyclopropyl)-4-(2'-formylbiphenyl-4-ylsulfonyl)-1-(1-(trifluoromethyl)cyclopropanecarbonyl)pyrrolidine-2-carboxamide;

(2S,4R)—N-(1-cyanocyclopropyl)-4-(2'-ethoxybiphenyl-4-ylsulfonyl)-1-(1-(trifluoromethyl)cyclopropanecarbonyl)pyrrolidine-2-carboxamide;

(2S,4R)-4-(4-(2-aminopyrimidin-5-yl)phenylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(2'-ethoxy-3-methylbiphenyl-4-ylsulfonyl)-1-(1-(trifluoromethyl)cyclopropanecarbonyl)pyrrolidine-2-carboxamide;

(2S,4R)-4-(2'-cyano-3-methylbiphenyl-4-ylsulfonyl)-N-(1-cyanocyclopropyl)-1-(1-(trifluoromethyl)cyclopropanecarbonyl)pyrrolidine-2-carboxamide;

(2S,4R)—N-(1-cyanocyclopropyl)-4-(2'-ethoxy-4',5'-difluoro-3-methylbiphenyl-4-ylsulfonyl)-1-(1-(trifluoromethyl)cyclopropanecarbonyl)pyrrolidine-2-carboxamide;

(2S,4R)—N-(1-cyanocyclopropyl)-4-(2'-(hydroxymethyl)biphenyl-4-ylsulfonyl)-1-(1-(trifluoromethyl)cyclopropanecarbonyl)pyrrolidine-2-carboxamide;

(2S,4R)-4-(4-(2-aminopyrimidin-5-yl)-2-methylphenylsulfonyl)-N-(1-cyanocyclopropyl)-1-(1-(trifluoromethyl)cyclopropanecarbonyl)pyrrolidine-2-carboxamide;

(2S,4R)-4-[4-(2,2-Difluoro-benzo[1,3]dioxol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-1-(1-Trifluoromethyl-cyclopropanecarbonyl)-4-[2-trifluoromethyl-4-(4-trifluoromethyl-pyrazol-1-yl)-benzenesulfonyl]-pyrrolidine-2-carboxylic acid (1-cyano-cyclopropyl)-amide;

(2S,4R)-4-[4-(5-Methyl-tetrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(2,4-Dimethyl-thiazol-5-yl)-2-trifluoromethyl-benzene sulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(2,4-dimethylthiazol-5-yl)phenylsulfonyl)-1-(1-(trifluoromethyl)cyclopropanecarbonyl)pyrrolidine-2-carboxamide;

(2S,4R)—N-(1-cyanocyclopropyl)-4-(4-(2-methylthiazol-5-yl)phenylsulfonyl)-1-(1-(trifluoromethyl)cyclopropanecarbonyl)pyrrolidine-2-carboxamide;

(2S,4R)—N-(1-cyanocyclopropyl)-4-(4-(2-methoxypyrimidin-5-yl)phenylsulfonyl)-1-(1-(trifluoromethyl)cyclopropanecarbonyl)pyrrolidine-2-carboxamide;

(2S,4R)-4-(2-chloro-4-(5-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;

(2S,4R)-4-(4-[1,2,3]Triazol-2-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(4-[1,2,3]Triazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(3,5-dimethyl-isoxazol-4-yl)phenyl sulfonyl)-1-(1-(trifluoromethyl)cyclopropanecarbonyl)pyrrolidine-2-carboxamide;

(2S,4R)-4-[4-(1-Difluoromethyl-1H-pyrazol-4-yl)-2-trifluoromethyl-benzene sulfonyl]-1-(1-trifluoromethyl-cyclopropanecarbonyl)-pyrrolidine-2-carboxylic acid (1-cyano-cyclopropyl)-amide;

(2S,4R)-4-[4-(5-Methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-1-(1-Trifluoromethyl-cyclopropanecarbonyl)-4-[2-trifluoromethyl-4-(3-trifluoromethyl-1H-pyrazol-4-yl)-benzenesulfonyl]-pyrrolidine-2-carboxylic acid (1-cyano-cyclopropyl)-amide;

(2S,4R)—N-(1-cyanocyclopropyl)-4-(2'-(hydroxymethyl)-3-methylbiphenyl-4-ylsulfonyl)-1-(1-(trifluoromethyl)cyclopropanecarbonyl)pyrrolidine-2-carboxamide;

(2S,4R)—N-(1-cyanocyclopropyl)-4-(4-(2,4-dimethyl-thiazol-5-yl)-2-methylphenylsulfonyl)-1-(1-(trifluoromethyl)cyclopropanecarbonyl)pyrrolidine-2-carboxamide;

(2S,4R)—N-(1-cyanocyclopropyl)-4-(2-methyl-4-(2-methylthiazol-5-yl)phenylsulfonyl)-1-(1-(trifluoromethyl)cyclopropanecarbonyl)pyrrolidine-2-carboxamide;

(2S,4R)—N-(1-cyanocyclopropyl)-4-(4-(2-methoxypyrimidin-5-yl)-2-methylphenylsulfonyl)-1-(1-(trifluoromethyl)cyclopropanecarbonyl)pyrrolidine-2-carboxamide;

(2S,4R)-4-[4-(2-Methyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)—N-(1-cyanocyclopropyl)-4-(4-(3,5-dimethyl-isoxazol-4-yl)-2-methylphenylsulfonyl)-1-(1-(trifluoromethyl)cyclopropanecarbonyl)pyrrolidine-2-carboxamide;

(2S,4R)-4-(4-Tetrazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(4-(3-chloro-1H-1,2,4-triazol-1-yl)-2-methyl-phenylsulfonyl)-N-(1-cyanocyclopropyl)-1-(1-(trifluoromethyl)cyclopropanecarbonyl)pyrrolidine-2-carboxamide;

(2R,4R)-4-(4-(3-chloro-1H-1,2,4-triazol-1-yl)-2-methyl-phenylsulfonyl)-N-(1-cyanocyclopropyl)-1-(1-(trifluoromethyl)cyclopropanecarbonyl)pyrrolidine-2-carboxamide;

(2S,4R)-4-[4-(1-Methyl-3-trifluoromethyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide; and (2S,4R)-4-(4-(3-chloro-1H-1,2,4-triazol-1-yl)phenyl sulfonyl)-N-(1-cyanocyclopropyl)-1-(1-(trifluoromethyl)cyclopropanecarbonyl)pyrrolidine-2-carboxamide;

or a pharmaceutically acceptable salt or ester thereof.

7. A compound according to claim 1, selected from
(2S,4R)-4-[4-(2-Methyl-5-trifluoromethyl-2H-pyrazol-3-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-(2-chloro-4-(5-methyl-2H-tetrazol-2-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(5-methyl-1H-tetrazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(1H-1,2,4-triazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(2H-1,2,3-triazol-2-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(1H-1,2,3-triazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(3-methyl-1H-1,2,4-triazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(3,5-dimethyl-1H-1,2,4-triazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(3-chloro-1H-1,2,4-triazol-1-yl)phenyl sulfonyl)-N-(1-cyanocyclopropyl)-1-(1-(trifluoromethyl)cyclopropanecarbonyl)pyrrolidine-2-carboxamide;
(2S,4R)-4-(2-chloro-4-(3-(trifluoromethyl)-1H-pyrazol-1-yl)phenyl sulfonyl)-N-(1-cyanocyclopropyl)-1-(1-(trifluoromethyl)cyclopropanecarbonyl)pyrrolidine-2-carboxamide;
2S,4R)-4-(2-chloro-4-(5-methyl-3 (trifluoromethyl)-1H-pyrazol-1-yl)phenylsulfonyl)-N-(1-cyanocyclopropyl)-1-(1-trifluoromethyl)cyclopropanecarbonyl)pyrrolidine-2-carboxamide;
(2S,4R)—N-(1-cyanocyclopropyl)-4-(2-methyl-4-(3-(trifluoromethyl)-1H-pyrazol-1-yl)phenyl sulfonyl)-1-(1-(trifluoromethyl)cyclopropanecarbonyl)pyrrolidine-2-carboxamide;
(2S,4R)-4-[4-(5-Methyl-3-trifluoromethyl-pyrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(3-Methyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(3-Methyl-[1,2,4]triazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-(4-(1H-1,2,4-triazol-1-yl)-2-(trifluoromethyl)phenyl sulfonyl)-N-(1-cyanocyclopropyl)-1-(1-(trifluoromethyl)cyclopropanecarbonyl)pyrrolidine-2-carboxamide;
(2S,4R)-4-[4-(3,5-Dimethyl-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(3-Chloro-[1,2,4]triazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)—N-(1-cyanocyclopropyl)-4-(4-(5-methyl-1H-1,2,4-triazol-1-yl)-2-(trifluoromethyl)phenylsulfonyl)-1-(1-(trifluoromethyl)cyclopropanecarbonyl)pyrrolidine-2-carboxamide;
(2S,4R)—N-(1-cyano cyclopropyl)-4-(2-methyl-4-(1-methyl-3-(trifluoromethyl)-1H-pyrazol-5-yl)phenyl sulfonyl-1-(1-(trifluoromethyl)cyclopropanecarbonyl) pyrrolidine-2-carboxamide;
(2S,4R)-1-(1-Trifluoromethyl-cyclopropanecarbonyl)-4-[2-trifluoromethyl-4-(4-trifluoromethyl-pyrazol-1-yl)-benzenesulfonyl]-pyrrolidine-2-carboxylic acid (1-cyano-cyclopropyl)-amide;
(2S,4R)-4-[4-(5-Methyl-tetrazol-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(2,4-Dimethyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-(2-chloro-4-(5-methyl-1H-1,2,4-triazol-1-yl)phenylsulfonyl)-N-(1-cyanocyclopropyl)-1-(1-(trifluoromethyl)cyclopropanecarbonyl)pyrrolidine-2-carboxamide;
(2S,4R)-4-(4-[1,2,3]Triazol-2-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;
(2S,4R)-4-(4-[1,2,3]Triazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;
(2S,4R)-4-[4-(1-Difluoromethyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-4-[4-(5-Methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)-1-(1-Trifluoromethyl-cyclopropanecarbonyl)-4-[2-trifluoromethyl-4-(3-trifluoromethyl-1H-pyrazol-4-yl)-benzenesulfonyl]-pyrrolidine-2-carboxylic acid (1-cyano-cyclopropyl)-amide;
(2S,4R)—N-(1-cyanocyclopropyl)-4-(4-(2,4-dimethyl-thiazol-5-yl)-2-methylphenylsulfonyl)-1-(1-(trifluoromethyl)cyclopropanecarbonyl)pyrrolidine-2-carboxamide;
(2S,4R)—N-(1-cyanocyclopropyl)-4-(2-methyl-4-(2-methylthiazol-5-yl)phenylsulfonyl)-1-(1-(trifluoromethyl)cyclopropanecarbonyl)pyrrolidine-2-carboxamide;
(2S,4R)-4-[4-(2-Methyl-thiazol-5-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;
(2S,4R)—N-(1-cyanocyclopropyl)-4-(4-(3,5-dimethyl-isoxazol-4-yl)-2-methylphenylsulfonyl)-1-(1-(trifluoromethyl)cyclopropanecarbonyl)pyrrolidine-2-carboxamide;
(2S,4R)-4-(4-Tetrazol-1-yl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(4-(3-chloro-1H-1,2,4-triazol-1-yl)-2-methyl-phenyl sulfonyl)-N-(1-cyanocyclopropyl)-1-(1-(trifluoromethyl)cyclopropanecarbonyl)pyrrolidine-2-carboxamide;

(2R,4R)-4-(4-(3-chloro-1H-1,2,4-triazol-1-yl)-2-methyl-phenylsulfonyl)-N-(1-cyanocyclopropyl)-1-(1-(trifluoromethyl)cyclopropanecarbonyl)pyrrolidine-2-carboxamide; and (2S,4R)-4-[4-(1-Methyl-3-trifluoromethyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

or a pharmaceutically acceptable salt or ester thereof.

8. A compound which is (2S,4R)-4-[4-(5-Methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt or ester thereof.

9. A process for the manufacture of a compound according to claim 1, or a pharmaceutically acceptable salt or ester thereof, comprising:

(a) The reaction of a compound of formula (A)

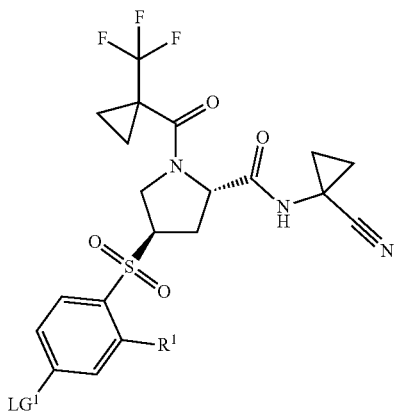

in the presence of a compound of formula $R^2$-$LG^2$, wherein $LG^1$ is selected from the group consisting of F, Cl, Br, I, $B(OH)_2$ and $B(OR^3)_2$;

$LG^2$ is selected from the group consisting of $B(OR)_2$, $B(OR^3)_2$, Br and I; and each $R^3$ substituent is independently selected from methyl and ethyl; or both $R^3$ substituents together with the oxygen and boron atoms to which they are attached form an organoboron ring; or (b) The reaction of a compound of formula (B)

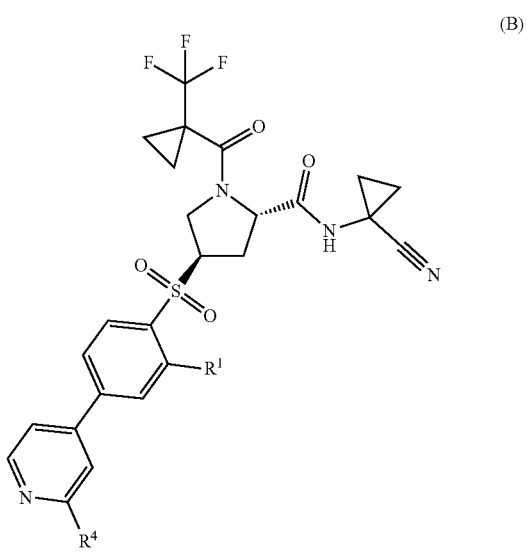

in the presence of oxidative conditions, wherein $R^4$ is halogen or alkyl.

10. A pharmaceutical composition comprising a compound according to claim 1, or a pharmaceutically acceptable salt or ester thereof, and a therapeutically inert carrier.

11. A method for the treatment or prophylaxis of diabetes, atherosclerosis, abdominal aortic aneurysm, peripheral arterial disease, reduction of cardiovascular events in chronic kidney disease, diabetic nephropathy, diabetic retinopathy or age related macular degeneration, which method comprises administering an effective amount of a compound according to claim 1, or a pharmaceutically acceptable salt or ester thereof, to a patient in need thereof.

12. The compound of claim 1, wherein
$R^1$ is haloalkyl; and
$R^2$ is alkyltetrazolyl.

13. The compound of claim 1, wherein
$R^1$ is methyl, trifluoromethyl or chlorine; and
$R^2$ is methyltetrazolyl.

14. The process of claim 9, wherein the compound of formula (B) is reacted in the presence of an oxidative reagent selected from the group consisting of hydrogen peroxide, meta-chloroperoxybenzoic acid and oxone.

15. The process of claim 9, wherein $LG^2$ is 4,4,5,5-tetramethyl-1,3,2-dioxaborolane.

16. A method for the treatment of tumor growth, which method comprises administering an effective amount of a compound according to claim 1, or a pharmaceutically acceptable salt or ester thereof, to a patient in need thereof.

* * * * *